(12) United States Patent
Winslow et al.

(10) Patent No.: US 7,591,851 B2
(45) Date of Patent: Sep. 22, 2009

(54) INTER-CERVICAL FACET IMPLANT AND METHOD

(75) Inventors: Charles J. Winslow, Walnut Creek, CA (US); James F. Zucherman, San Francisco, CA (US); Ken Y. Hsu, San Francisco, CA (US); Steven T. Mitchell, Pleasant Hill, CA (US); Scott A. Yerby, Montara, CA (US); John J. Flynn, West Milford, NJ (US)

(73) Assignee: Kyphon SARL (CH)

( * ) Notice: Subject to any disclaimer, the term of this patent is extended or adjusted under 35 U.S.C. 154(b) by 417 days.

(21) Appl. No.: 11/053,399

(22) Filed: Feb. 8, 2005

(65) Prior Publication Data

US 2006/0149373 A1    Jul. 6, 2006

Related U.S. Application Data

(60) Provisional application No. 60/635,453, filed on Dec. 13, 2004.

(51) Int. Cl.
  *A61F 2/44* (2006.01)
(52) U.S. Cl. .................... 623/17.11; 606/247
(58) Field of Classification Search ... 623/17.11–17.16; 606/61, 86, 90, 246–249
  See application file for complete search history.

(56) References Cited

U.S. PATENT DOCUMENTS

| | | | |
|---|---|---|---|
| 2,456,806 A | 12/1948 | Wolffe | |
| 2,677,369 A | 5/1954 | Knowles | |
| 3,426,364 A | 2/1969 | Lumb | |
| 3,643,658 A | 2/1972 | Steinemenan | |
| 3,648,691 A | 3/1972 | Lumb | |
| 3,867,728 A | 2/1975 | Stubstad | |
| 3,875,595 A | 4/1975 | Froning | |
| 3,879,767 A | 4/1975 | Stubstad | |
| 4,001,896 A | 1/1977 | Arkangel | |
| 4,034,418 A | 7/1977 | Jackson | |
| 4,085,466 A | 4/1978 | Goodfellow et al. | |
| 4,156,296 A | 5/1979 | Johnson et al. | |
| 4,219,015 A | 8/1980 | Steinemenan | |

(Continued)

FOREIGN PATENT DOCUMENTS

CA    2015507    1/1991

(Continued)

OTHER PUBLICATIONS

Minns, R.J., et al., *Preliminary Design and Experimental Studies of a Novel Soft Implant for Correcting Sagittal Plane Instability in the Lumbar Spine*, Spine vol. 22, No. 16, pp. 1819-1825, © 1997, Lippincott-Raven Publishers.

(Continued)

*Primary Examiner*—Thomas C Barrett
*Assistant Examiner*—Michael J Araj

(57) ABSTRACT

Systems and method in accordance with the embodiments of the present invention can include an implant for positioning within a cervical facet joint for distracting the cervical spine, thereby increasing the area of the canals and openings through which the spinal cord and nerves must pass, and decreasing pressure on the spinal cord and/or nerve roots. The implant can be inserted laterally or posteriorly.

21 Claims, 24 Drawing Sheets

U.S. PATENT DOCUMENTS

| | | |
|---|---|---|
| 4,231,121 A | 11/1980 | Lewis |
| 4,309,777 A | 1/1982 | Patil |
| 4,349,921 A | 9/1982 | Kuntz |
| 4,369,769 A | 1/1983 | Edwards |
| 4,401,112 A | 8/1983 | Rezaian |
| 4,455,690 A | 6/1984 | Homsy |
| 4,479,491 A | 10/1984 | Martin |
| 4,501,269 A | 2/1985 | Bagby |
| 4,553,273 A | 11/1985 | Wu |
| 4,554,914 A | 11/1985 | Kapp |
| 4,599,084 A | 7/1986 | Nashef |
| 4,599,086 A | 7/1986 | Doty |
| 4,604,995 A | 8/1986 | Stephens |
| 4,611,582 A | 9/1986 | Duff |
| 4,636,217 A | 1/1987 | Ogilvie |
| 4,643,178 A | 2/1987 | Nastari |
| 4,657,550 A | 4/1987 | Daher |
| 4,685,447 A | 8/1987 | Iversen |
| 4,696,290 A | 9/1987 | Steffee |
| 4,714,469 A | 12/1987 | Kenna |
| 4,743,256 A | 5/1988 | Brantigan |
| 4,759,769 A | 7/1988 | Hedman et al. |
| 4,772,287 A | 9/1988 | Ray |
| 4,790,303 A | 12/1988 | Steffee |
| 4,834,757 A | 5/1989 | Brantigan |
| 4,502,161 A | 7/1989 | Wall |
| 4,863,477 A | 9/1989 | Monson |
| 4,878,915 A | 11/1989 | Brantigan |
| 4,904,260 A | 2/1990 | Ray |
| 4,904,261 A | 2/1990 | Dove |
| 4,911,718 A | 3/1990 | Lee et al. |
| 4,913,134 A | 4/1990 | Luque |
| 4,923,471 A | 5/1990 | Morgan |
| 4,932,975 A | 6/1990 | Main |
| 4,936,848 A | 6/1990 | Bagby |
| 4,946,378 A | 8/1990 | Hirayama |
| 4,961,740 A | 10/1990 | Ray |
| 4,969,888 A | 11/1990 | Scholten |
| 5,011,484 A | 4/1991 | Breard |
| 5,015,247 A | 5/1991 | Michelson |
| 5,015,255 A | 5/1991 | Kuslich |
| 5,026,373 A | 6/1991 | Ray |
| 5,035,716 A | 7/1991 | Downey |
| 5,047,055 A | 9/1991 | Bao |
| 5,055,104 A | 10/1991 | Ray |
| 5,059,193 A | 10/1991 | Kuslich |
| 5,059,194 A | 10/1991 | Michelson |
| 5,062,845 A | 11/1991 | Kuslich |
| 5,062,850 A | 11/1991 | MacMillan |
| 5,071,437 A | 12/1991 | Steffee |
| 5,074,864 A | 12/1991 | Cozad |
| 5,084,049 A | 1/1992 | Asher et al. |
| 5,088,869 A | 2/1992 | Greenslade |
| 5,092,866 A | 3/1992 | Breard |
| 5,105,255 A | 4/1992 | Shannon |
| 5,122,130 A | 6/1992 | Keller |
| 5,123,926 A | 6/1992 | Pisharodi |
| 5,127,912 A | 7/1992 | Ray |
| 5,147,404 A | 9/1992 | Downey |
| 5,167,662 A | 12/1992 | Hayes |
| 5,167,665 A | 12/1992 | McKinney |
| 5,171,280 A | 12/1992 | Baumgartner |
| 5,180,381 A | 1/1993 | Aust |
| 5,192,326 A | 3/1993 | Bao et al. |
| 5,192,327 A | 3/1993 | Brantigan |
| 5,258,031 A | 11/1993 | Salib |
| 5,263,953 A | 11/1993 | Bagby |
| 5,275,601 A | 1/1994 | Gogolewski |
| 5,290,312 A | 3/1994 | Kojimoto |
| 5,300,073 A | 4/1994 | Ray |
| 5,304,178 A | 4/1994 | Stahurski |
| 5,306,275 A | 4/1994 | Bryan |
| 5,306,308 A | 4/1994 | Gross et al. |
| 5,306,309 A | 4/1994 | Wagner |
| 5,352,225 A | 10/1994 | Yuan |
| 5,360,431 A | 11/1994 | Puno et al. |
| 5,366,455 A | 11/1994 | Dove |
| 5,370,697 A | 12/1994 | Baumgartner |
| 5,387,213 A | 2/1995 | Breard |
| 5,390,683 A | 2/1995 | Pisharodi |
| 5,391,168 A | 2/1995 | Sanders |
| 5,395,372 A | 3/1995 | Holt |
| 5,401,269 A | 3/1995 | Buttner-Janz et al. |
| 5,415,659 A * | 5/1995 | Lee et al. ..................... 606/61 |
| 5,415,661 A | 5/1995 | Holmes |
| 5,425,773 A | 6/1995 | Boyd et al. |
| 5,437,672 A | 8/1995 | Alleyne |
| 5,443,514 A | 8/1995 | Steffee |
| 5,445,639 A | 8/1995 | Kuslich et al. |
| 5,454,812 A | 10/1995 | Lin |
| 5,456,722 A | 10/1995 | McLeod |
| 5,458,638 A | 10/1995 | Kuslich |
| 5,458,641 A | 10/1995 | Ramirez Jimenez |
| 5,458,642 A | 10/1995 | Beer et al. |
| 5,458,643 A | 10/1995 | Oka |
| 5,468,242 A | 11/1995 | Reisberg |
| 5,470,333 A | 11/1995 | Ray |
| 5,491,882 A | 2/1996 | Walston |
| 5,496,318 A | 3/1996 | Howland |
| 5,505,732 A | 4/1996 | Michelson |
| 5,507,745 A | 4/1996 | Logroscino |
| 5,507,823 A | 4/1996 | Walston |
| 5,514,180 A | 5/1996 | Heggeness |
| 5,527,312 A | 6/1996 | Ray |
| 5,527,314 A | 6/1996 | Brumfield et al. |
| 5,531,747 A | 7/1996 | Ray |
| 5,534,028 A | 7/1996 | Bao |
| 5,534,029 A | 7/1996 | Shima |
| 5,534,030 A | 7/1996 | Navarro et al. |
| 5,540,689 A | 7/1996 | Sanders |
| 5,545,229 A | 8/1996 | Parsons et al. |
| 5,549,679 A | 8/1996 | Kuslich |
| 5,554,191 A | 9/1996 | Lahille |
| 5,556,431 A | 9/1996 | Buttner-Janz |
| 5,562,736 A | 10/1996 | Ray |
| 5,562,738 A | 10/1996 | Boyd et al. |
| 5,571,189 A | 11/1996 | Kuslich |
| 5,571,191 A | 11/1996 | Fitz |
| 5,577,995 A | 11/1996 | Walker |
| 5,584,832 A | 12/1996 | Schlapfer |
| 5,591,165 A | 1/1997 | Jackson |
| 5,593,409 A | 1/1997 | Michelson |
| 5,601,553 A | 2/1997 | Trebing |
| 5,603,713 A | 2/1997 | Aust |
| 5,609,634 A | 3/1997 | Voydeville |
| 5,616,142 A | 4/1997 | Yuan |
| 5,623,984 A | 4/1997 | Nozaki |
| 5,628,756 A | 5/1997 | Barker, Jr. |
| 5,645,597 A | 7/1997 | Krapiva |
| 5,645,599 A | 7/1997 | Samani |
| 5,653,761 A | 8/1997 | Pisharodi |
| 5,653,762 A | 8/1997 | Pisharodi |
| 5,658,286 A | 8/1997 | Sava |
| 5,672,177 A | 9/1997 | Seldin |
| 5,674,295 A | 10/1997 | Ray |
| 5,674,296 A | 10/1997 | Bryan |
| 5,676,701 A | 10/1997 | Yuan et al. |
| 5,676,702 A | 10/1997 | Ratron |
| 5,683,464 A | 11/1997 | Wagner et al. |
| 5,702,450 A | 12/1997 | Bisserie |
| 5,702,455 A | 12/1997 | Saggar |
| 5,716,415 A | 2/1998 | Steffee |
| 5,725,582 A | 3/1998 | Bevan |
| 5,741,261 A | 4/1998 | Moskovitz |

| | | | | | | |
|---|---|---|---|---|---|---|
| 5,766,251 A | 6/1998 | Koshino | | 6,565,570 B2 | 5/2003 | Sterett |
| 5,766,252 A | 6/1998 | Henry | | 6,565,605 B2 | 5/2003 | Goble |
| 5,766,253 A | 6/1998 | Brosnahan, III | | 6,572,653 B1 | 6/2003 | Simonson |
| 5,800,438 A | 9/1998 | Tuke | | 6,579,318 B2 | 6/2003 | Varga |
| 5,824,093 A | 10/1998 | Ray et al. | | 6,579,319 B2 | 6/2003 | Goble |
| 5,824,094 A | 10/1998 | Serhan et al. | | 6,592,586 B1 | 7/2003 | Michelson |
| 5,824,098 A | 10/1998 | Stein | | 6,610,091 B1 | 8/2003 | Reiley |
| 5,836,948 A | 11/1998 | Zucherman | | 6,620,163 B1 | 9/2003 | Michelson |
| 5,860,977 A | 1/1999 | Zucherman | | 6,669,729 B2 | 12/2003 | Chin |
| 5,865,846 A | 2/1999 | Bryan | | 6,712,852 B1 | 3/2004 | Chung |
| 5,868,745 A | 2/1999 | Alleyne | | 6,730,127 B2 | 5/2004 | Michelson |
| 5,876,402 A | 3/1999 | Errico | | 6,752,831 B2 | 6/2004 | Sybert |
| 5,876,404 A | 3/1999 | Zucherman | | 6,761,720 B1 | 7/2004 | Senegas |
| 5,879,396 A | 3/1999 | Walston | | 6,764,491 B2 | 7/2004 | Frey et al. |
| 5,885,299 A | 3/1999 | Winslow | | 6,783,527 B2 | 8/2004 | Drewry |
| 5,888,224 A | 3/1999 | Beckers | | 6,800,670 B2 | 10/2004 | Shen |
| 5,888,226 A | 3/1999 | Rogozinski | | 6,811,567 B2 | 11/2004 | Reiley |
| 5,893,889 A | 4/1999 | Harrington | | 6,902,566 B2 | 6/2005 | Zucherman et al. |
| RE36,221 E | 6/1999 | Breard et al. | | 6,974,478 B2 | 12/2005 | Reiley et al. |
| 5,951,555 A | 9/1999 | Rehak | | 7,101,375 B2 | 9/2006 | Zucherman et al. |
| 5,976,186 A | 11/1999 | Bao | | 2001/0012938 A1 | 8/2001 | Zucherman |
| 6,001,130 A | 12/1999 | Bryan | | 2001/0018614 A1 | 8/2001 | Bianchi |
| 6,014,588 A | 1/2000 | Fitz | | 2002/0004683 A1 | 1/2002 | Michelson |
| 6,019,792 A | 2/2000 | Cauthen | | 2002/0016595 A1 | 2/2002 | Michelson |
| 6,022,376 A | 2/2000 | Assell | | 2002/0022843 A1 | 2/2002 | Michelson |
| 6,030,162 A | 2/2000 | Huebner | | 2002/0029039 A1 | 3/2002 | Zucherman et al. |
| 6,039,763 A | 3/2000 | Shelokov | | 2002/0065557 A1 | 5/2002 | Goble |
| 6,045,554 A | 4/2000 | Grooms | | 2002/0072800 A1 | 6/2002 | Goble |
| 6,048,204 A | 4/2000 | Klardie | | 2002/0077700 A1 | 6/2002 | Varga |
| 6,048,342 A | 4/2000 | Zucherman | | 2002/0099376 A1 | 7/2002 | Michelson |
| 6,048,344 A | 4/2000 | Schenk | | 2002/0128655 A1 | 9/2002 | Michelson |
| 6,063,121 A | 5/2000 | Xavier et al. | | 2002/0133155 A1 | 9/2002 | Ferree |
| 6,066,325 A | 5/2000 | Wallace et al. | | 2002/0151895 A1 | 10/2002 | Soboleski |
| 6,068,630 A | 5/2000 | Zucherman | | 2002/0183756 A1 | 12/2002 | Michelson |
| RE36,758 E | 6/2000 | Fitz | | 2002/0183757 A1 | 12/2002 | Michelson |
| 6,080,157 A | 6/2000 | Cathro et al. | | 2002/0188296 A1 | 12/2002 | Michelson |
| 6,099,531 A | 8/2000 | Bonutti | | 2003/0004572 A1 | 1/2003 | Goble |
| 6,113,637 A | 9/2000 | Gill et al. | | 2003/0028250 A1 | 2/2003 | Reiley |
| 6,113,639 A | 9/2000 | Ray | | 2003/0040746 A1 | 2/2003 | Mitchell |
| 6,129,730 A | 10/2000 | Bono | | 2003/0060828 A1 | 3/2003 | Michelson |
| 6,132,464 A | 10/2000 | Martin | | 2003/0078668 A1 | 4/2003 | Michelson |
| 6,132,465 A | 10/2000 | Ray et al. | | 2003/0181912 A1 | 9/2003 | Michelson |
| 6,139,550 A | 10/2000 | Michelson | | 2003/0187454 A1 | 10/2003 | Gill et al. |
| 6,152,927 A | 11/2000 | Farris | | 2003/0191471 A1 | 10/2003 | Michelson |
| 6,156,067 A | 12/2000 | Bryan | | 2003/0191472 A1 | 10/2003 | Michelson |
| 6,190,414 B1 | 2/2001 | Young | | 2003/0191532 A1 | 10/2003 | Goble |
| 6,193,721 B1 | 2/2001 | Michelson | | 2003/0204259 A1 | 10/2003 | Goble |
| 6,200,322 B1 | 3/2001 | Branch | | 2004/0006391 A1 | 1/2004 | Reiley |
| 6,206,922 B1 | 3/2001 | Zdeblick | | 2004/0049272 A1 | 3/2004 | Reiley |
| 6,217,580 B1 | 4/2001 | Levin | | 2004/0049273 A1 | 3/2004 | Reiley |
| 6,224,602 B1 | 5/2001 | Hayes | | 2004/0049274 A1 | 3/2004 | Reiley |
| 6,224,607 B1 | 5/2001 | Michelson | | 2004/0049275 A1 | 3/2004 | Reiley |
| 6,228,900 B1 | 5/2001 | Shen | | 2004/0049276 A1 | 3/2004 | Reiley |
| 6,234,705 B1 | 5/2001 | Troxell | | 2004/0049277 A1 | 3/2004 | Reiley |
| 6,261,296 B1 | 7/2001 | Aebi et al. | | 2004/0049278 A1 | 3/2004 | Reiley |
| 6,293,949 B1 | 9/2001 | Justis | | 2004/0049281 A1 | 3/2004 | Reiley |
| 6,306,136 B1 | 10/2001 | Baccelli | | 2004/0059429 A1 | 3/2004 | Amin et al. |
| 6,352,537 B1 | 3/2002 | Strnad | | 2004/0087948 A1 | 5/2004 | Suddaby |
| 6,368,351 B1 | 4/2002 | Glenn | | 2004/0111154 A1 | 6/2004 | Reiley |
| 6,383,186 B1 | 5/2002 | Michelson | | 2004/0116927 A1 | 6/2004 | Graf |
| 6,395,030 B1 | 5/2002 | Songer | | 2004/0122427 A1 | 6/2004 | Holmes |
| 6,398,783 B1 | 6/2002 | Michelson | | 2004/0127989 A1 | 7/2004 | Dooris |
| 6,402,756 B1 | 6/2002 | Ralph | | 2004/0143264 A1 | 7/2004 | McAfee |
| 6,419,703 B1 | 7/2002 | Fallin | | 2004/0143268 A1 | 7/2004 | Falahee |
| 6,428,542 B1 | 8/2002 | Michelson | | 2004/0181226 A1 | 9/2004 | Michelson |
| 6,436,101 B1 | 8/2002 | Hamada | | 2004/0181229 A1 | 9/2004 | Michelson |
| 6,436,145 B1 | 8/2002 | Miller | | 2004/0186475 A1 | 9/2004 | Falahee |
| 6,454,771 B1 | 9/2002 | Michelson | | 2004/0186476 A1 | 9/2004 | Michelson |
| 6,458,131 B1 | 10/2002 | Ray | | 2004/0210313 A1 | 10/2004 | Michelson |
| 6,470,207 B1 | 10/2002 | Simon et al. | | 2004/0210314 A1 | 10/2004 | Michelson |
| 6,527,776 B1 | 3/2003 | Michelson | | 2004/0215195 A1 | 10/2004 | Shipp et al. |
| 6,558,423 B1 | 5/2003 | Michelson | | 2004/0220678 A1 | 11/2004 | Chow |
| 6,558,686 B1 | 5/2003 | Darouiche | | 2004/0230201 A1 | 11/2004 | Yuan |

| | | | |
|---|---|---|---|
| 2004/0230304 A1 | 11/2004 | Yuan | |
| 2004/0236334 A1 | 11/2004 | Michelson | |
| 2004/0236335 A1 | 11/2004 | Michelson | |
| 2005/0010291 A1 | 1/2005 | Stinson et al. | |
| 2005/0027297 A1 | 2/2005 | Michelson | |
| 2005/0027298 A1 | 2/2005 | Michelson | |
| 2005/0049705 A1 | 3/2005 | Hale et al. | |
| 2005/0131538 A1* | 6/2005 | Chervitz et al. | 623/17.11 |
| 2005/0159746 A1 | 7/2005 | Grob et al. | |
| 2005/0187551 A1 | 8/2005 | Orbay et al. | |
| 2005/0228381 A1* | 10/2005 | Kirschman | 606/61 |
| 2006/0036243 A1* | 2/2006 | Sasso et al. | 606/61 |
| 2006/0036323 A1* | 2/2006 | Carl et al. | 623/17.11 |
| 2006/0084984 A1* | 4/2006 | Kim | 606/61 |
| 2006/0085076 A1* | 4/2006 | Krishna et al. | 623/17.15 |
| 2006/0111780 A1* | 5/2006 | Petersen | 623/17.11 |
| 2006/0111781 A1* | 5/2006 | Petersen | 623/17.11 |

FOREIGN PATENT DOCUMENTS

| | | |
|---|---|---|
| DE | 2821678 A1 | 4/1980 |
| DE | 3113142 A1 | 1/1982 |
| DE | 4012622 C1 | 7/1991 |
| DE | 9304368 U | 6/1993 |
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |
| EP | 0307241 B1 | 12/1992 |
| EP | 0677277 A2 | 10/1995 |
| EP | 0767636 B1 | 4/1997 |
| EP | 1138268 A1 | 10/2001 |
| FR | 2623085 | 5/1989 |
| FR | 2681525 A1 | 3/1993 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2722088 | 1/1996 |
| FR | 2722980 A1 | 2/1996 |
| FR | 2724554 | 3/1996 |
| FR | 2780269 A1 | 12/1999 |
| FR | 2782911 A1 | 3/2000 |
| FR | 2806614 A1 | 9/2001 |
| FR | 2806616 A1 | 9/2001 |
| GB | 780652 | 8/1957 |
| JP | 10-179622 | 7/1998 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 94/26193 | 11/1994 |
| WO | WO 95/35067 | 12/1995 |
| WO | WO 96/08206 A1 | 3/1996 |
| WO | WO 96/39975 | 12/1996 |
| WO | WO 98/48717 | 11/1998 |
| WO | WO 98/55038 | 12/1998 |
| WO | WO 99/23963 A1 | 5/1999 |
| WO | WO 99/26562 | 6/1999 |
| WO | WO 99/40866 | 8/1999 |
| WO | WO 99/42051 | 8/1999 |
| WO | WO 99/56653 | 11/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/38582 | 7/2000 |
| WO | WO 00/53126 | 9/2000 |
| WO | WO 01/26566 A1 | 4/2001 |
| WO | WO 01/28442 A1 | 4/2001 |
| WO | WO 01/30248 A1 | 5/2001 |
| WO | WO 02/34120 A2 | 5/2002 |
| WO | WO 02/085226 A1 | 10/2002 |
| WO | WO 03/057055 A1 | 7/2003 |
| WO | WO 03/101350 A1 | 12/2003 |
| WO | WO 2004/071358 A1 | 8/2004 |
| WO | WO 2004/098465 A1 | 11/2004 |

OTHER PUBLICATIONS

Waldemar Link, brochure entitled *Wirbelsäulen-Chirurgie: Instrumentarium Und Implantate Zur Wirbelsäulen-Chirurgie* (Spinal Surgery: Instrumentation and Implants for Spinal Surgery), Waldemar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77-86, © 1990 Raven Press, Ltd., New York.

Richard W. Porter, MD, FRCS, FRCSE, *Spinal Stenosis and Neurogenic Claudication*, Spine vol. 21, No. 17, pp. 2046-2052, © 1996, Lippincott-Raven Publishers.

Kirkaldy-Willis, W.H., et al., "Pathology and Pathogenesis of Lumbar Spondylosis and Stenosis," Spine, vol. 3, No. 4, Dec. 1978, pp. 319-328.

Kotani, Y., et al., "The effects of spinal fixation and destabilization on the biomechanical and histologic properties of spinal ligaments: An in vivo study," Spine, vol. 23, No. 6, Mar. 15, 1998, pp. 672-682.

Lemaire, J.P., et al., "Intervertebral disc prosthesis: results and prospects for the year 2000," Clinical Orthopaedics and Related Research, No. 337, 1997, pp. 64-76.

Lombardi, J.S., et al., "Treatment of Degenerative Spondylolisthesis," Spine, vol. 10, No. 9, 1985, pp. 821-827.

McMillin, C.R. et al., "Artificial Spinal Discs with up to Five Years Follow-up," 20th Annual Meeting of the Society for Biomaterials (Abstract), Apr. 5-9, 1994, pp. 89.

Nagata, H., et al., "The effects of immobilization of long segments of the spine on the adjacent and distal facet force and lumbosacral motion," Spine, vol. 18, No. 16, 1993, pp. 2471-2479.

Posner, I., et al., "A Biomechanical Analysis of the Clinical Stability of the Lumbar and Lumbosacral Spine," Spine, vol. 7, No. 4, 1982, pp. 374-389.

Rosenberg, N.J., "Degenerative Spondylolisthesis—Predisposing Factors," The Journal of Bone and Joint Surgery, vol. 57-A, No. 4, 1975, pp. 467-474.

Szpalski, M., et al., "Spine Arthroplasty: A Historical Review," Eur Spine J., vol. 11, Suppl. 2, Aug. 13, 2002, pp. S65-S84.

Tsantrizos, A., et al., "Segmental stability and compressive strength of posterior lumbar interbody fusion implants," Spine, vol. 25, No. 15, 2000, pp. 1899-1907.

Dickson, R.A., "The etiology and pathogenesis of idiopathic scoliosis," Acta Orthopaedica Belgica, vol. 58, Suppl. 1, 1992, pp. 21-25.

Dickson, R.A., "The scientific basis of treatment of idiopathic thoracic scoliosis," Acta Orthopaedica Belgica, vol. 58, Suppl.1, 1992, pp. 107-110.

Millner, P.A., et al., "Idiopathic scoliosis: biomechanics and biology," Eur. Spine J., vol. 5, 1996, pp. 362-373.

Mohaideen, A., et al., "Not all rods are Harrington—an overview of spinal instrumentation in scoliosis treatment," Pediatr. Radiol. 30, 2000, pp. 110-118.

Smith, R.M., et al., "Experimental structural scoliosis," The Journal of Bone and Joint Surgery, vol. 69, 1987, pp. 576-581.

Chiu, J.C., et al., "Translaminar Facet Fixation: An Alternative Method for Lumbar Fusion: Report of 710 Cases," http://www.spinecenter.com/papers/facet/facet.htm, Sep. 8, 2005, 12 pages.

Van Schaik, Jan P.J., et al., "Curvature of the Lower Lumbar Facet Joints: Variations at Different Levels and Relationship with Orientation," Journal of Spinal Disorders, vol. 12, No. 4, 1999, pp. 341-347.

Lu, J., et al.,"Translaminar Facet Screw Placement: an Anatomic Study," The American Journal of Orthopedics, Aug. 1998, pp. 550-555.

Ebraheim, N.A., et al.,"The Quantitative Anatomy of the Thoracic Facet and the Posterior Projection of Its Inferior Facet," Spine, vol. 22, No. 16, 1997, pp. 1811-1818.

Panjabi, M.M., et al.,"Articular Facets of the Human Spine, Quantitative Three-Dimensional Anatomy," Spine, vol. 18, No. 10, 1993, pp. 1298-1310.

Boden, S.D., et al., "Orientation of the Lumbar Facet Joints: Association with Degenerative Disc Disease," The Journal Of Bone and Joint Surgery, vol. 78-A, No. 3, Mar. 1996, pp. 403-411.

Cavanaugh, J.M., et al., "Lumbar Facet Pain: Biomechanics Neuroanatomy and Neurophysiology," Survey Article, J. Biomechanics, vol. 29, No. 9, 1996, pp. 1117-1129.

Yoganandan, N., et al.,"Anatomic Study of the Morphology of Human Cervical Facet Joint," Spine, vol. 28, No. 20, 2003, pp. 2317-2323.

Dudley, et al., "Spinal Injuries," Rod & Smith's Operative Surgery—Orthopaedics Part 1, London: Butterworth-Heinemann, 1991, pp. 637-641.

* cited by examiner

INTER-CERVICAL FACET IMPLANT AND METHOD

CLAIM OF PRIORITY

This application claims priority to United States Provisional Application, entitled, INTER-CERVICAL FACET IMPLANT AND METHOD filed Dec. 13, 2004, Ser. No. 60/635,453, which is incorporated herein by reference.

CROSS-REFERENCE TO RELATED APPLICATIONS

This application is related to U.S. patent application Ser. No. 11/053,624, entitled INTER-CERVICAL FACET IMPLANT AND METHOD, filed Feb. 8, 2005; U.S. patent application Ser. No. 11/053,735, entitled INTER-CERVICAL FACET IMPLANT AND METHOD, filed Feb. 8, 2005; and U.S. patent application Ser. No. 11/053,346, entitled INTER-CERVICAL FACET IMPLANT AND METHOD, filed Feb. 8, 2005 which are each incorporated herein in full, by reference.

TECHNICAL FIELD

This invention relates to interspinous process implants.

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area (i.e., the available space for the passage of nerves and blood vessels) which compresses the cervical nerve roots and causes radicular pain. Humpreys, S. C. et al., *Flexion and traction effect on C5-C6 foraminal space*, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression, and neural injury. Id.; Yoo, J. U. et al., *Effect of cervical spine motion on the neuroforaminal dimensions of human cervical spine*, Spine, vol. 17 at 1131 (Nov. 10, 1992). In contrast, neck flexion increases the foraminal area. Humpreys, S. C. et al., supra, at 1105.

In particular, cervical radiculopathy secondary to disc herniation and cervical spondylotic foraminal stenosis typically affects patients in their fourth and fifth decade, and has an annual incidence rate of 83.2 per 100,000 people (based on 1994 information). Cervical radiculopathy is typically treated surgically with either an anterior cervical discectomy and fusion ("ACDF") or posterior laminoforaminotomy ("PLD"), with or without facetectomy. ACDF is the most commonly performed surgical procedure for cervical radiculopathy, as it has been shown to increase significantly the foraminal dimensions when compared to a PLF.

It is desirable to eliminate the need for major surgery for all individuals, and in particular, for the elderly. Accordingly, a need exists to develop spine implants that alleviate pain caused by spinal stenosis and other such conditions caused by damage to, or degeneration of, the cervical spine.

DETAILED DESCRIPTION

Embodiments of the present invention provide for a minimally invasive surgical implantation method and apparatus for cervical spine implants that preserves the physiology of the spine. In particular, embodiments provide for distracting the cervical spine to increase the foraminal dimension in extension and neutral positions. Such implants distract, or increase the space between, the vertebrae to increase the foraminal area or dimension, and reduce pressure on the nerves and blood vessels of the cervical spine. In a specific preferred embodiment, an implanted interfacet spacer of 1.5 mm to 2.5 mm in width can result in interfacet distraction that increases foraminal dimension in extension and neutral. Other interfacet spacer dimensions also are contemplated by the invention described herein below. The present embodiments also preserve mobility of the facet joints.

Further embodiments of the present invention accommodate the distinct anatomical structures of the spine, minimize further trauma to the spine, and obviate the need for invasive methods of surgical implantation. Embodiments of the present invention also address spinal conditions that are exacerbated by spinal extension.

Figure 1:
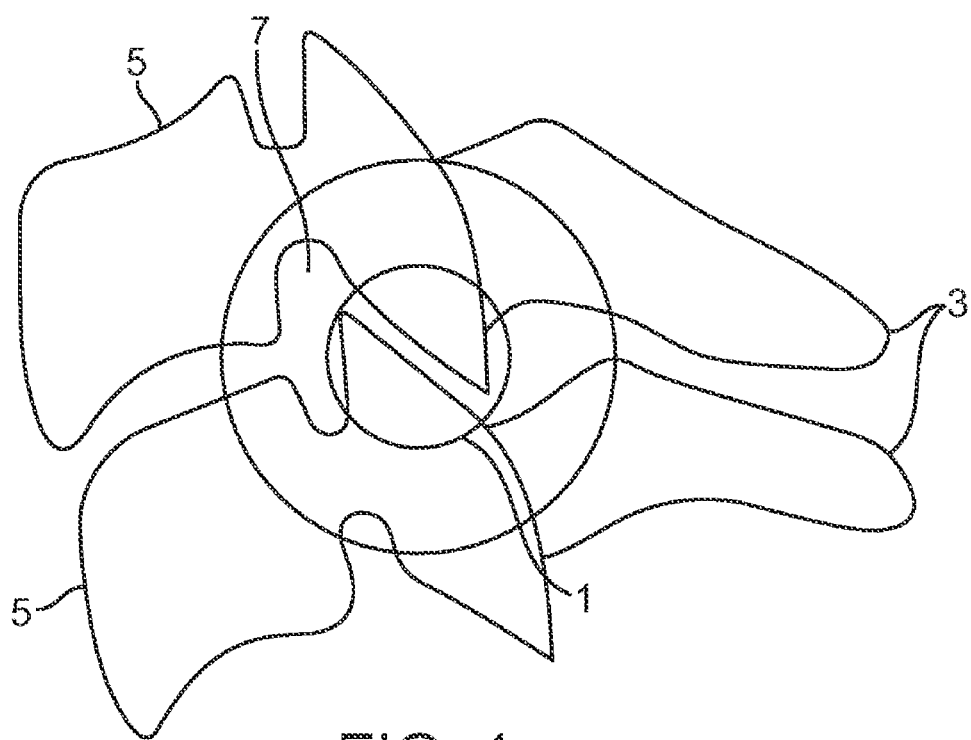
FIG. 1 shows a lateral view of two adjacent cervical vertebrae and spinous processes, highlighting the cervical facet joint.

FIG. 1 shows a simplified diagram of a portion of the cervical spine, focusing on a cervical facet joint 1 formed between two adjacent cervical vertebrae. The spinous processes 3 are located posteriorly and the vertebral bodies 5 are located anteriorly, and a nerve root canal 7 is visible.

Figure 2:
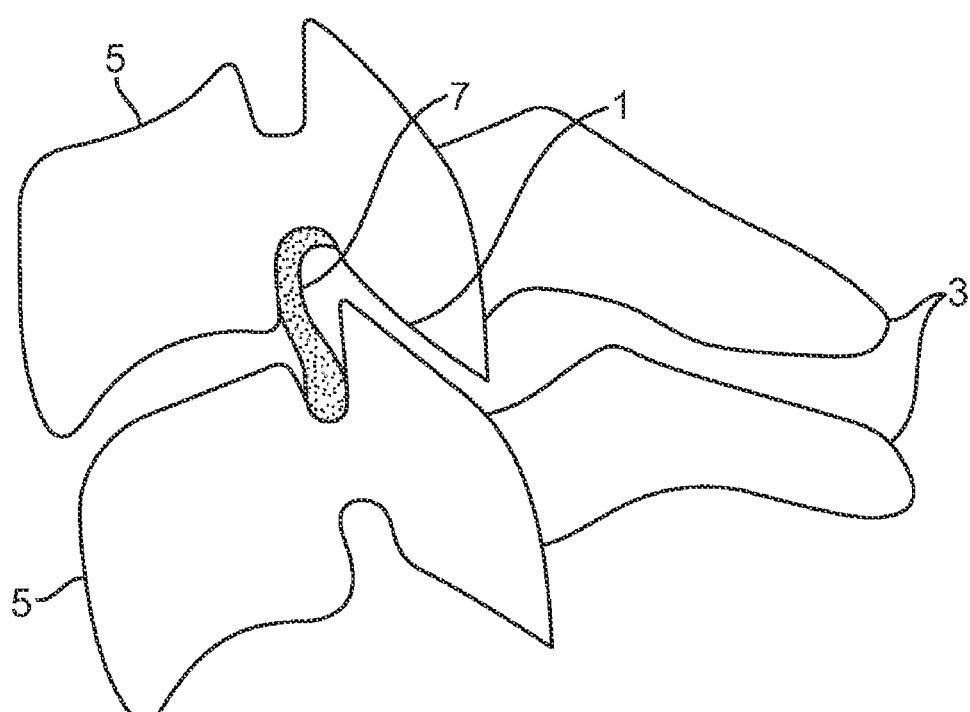
FIG. 2 depicts a lateral view of the cervical spine with spinal stenosis.

FIG. 2 depicts cervical foraminal stenosis. From the drawing, the nerve root canal 7 is narrowed relative to the nerve root canal 7 depicted in FIG. 1. The spinal canal and/or intervertebral foraminal also can be narrowed by stenosis. The narrowing can cause compression of the spinal cord and nerve roots.

Figure 3A:
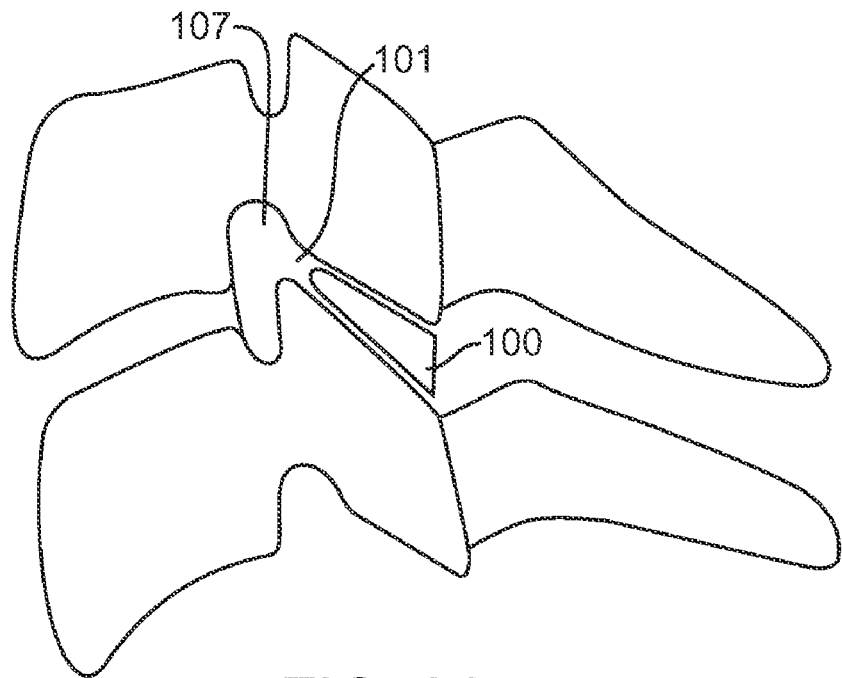
FIG. 3A depicts correction of cervical stenosis or other ailment with a wedge-shaped embodiment of the implant of the invention positioned in the cervical facet joint.
Figure 3B:
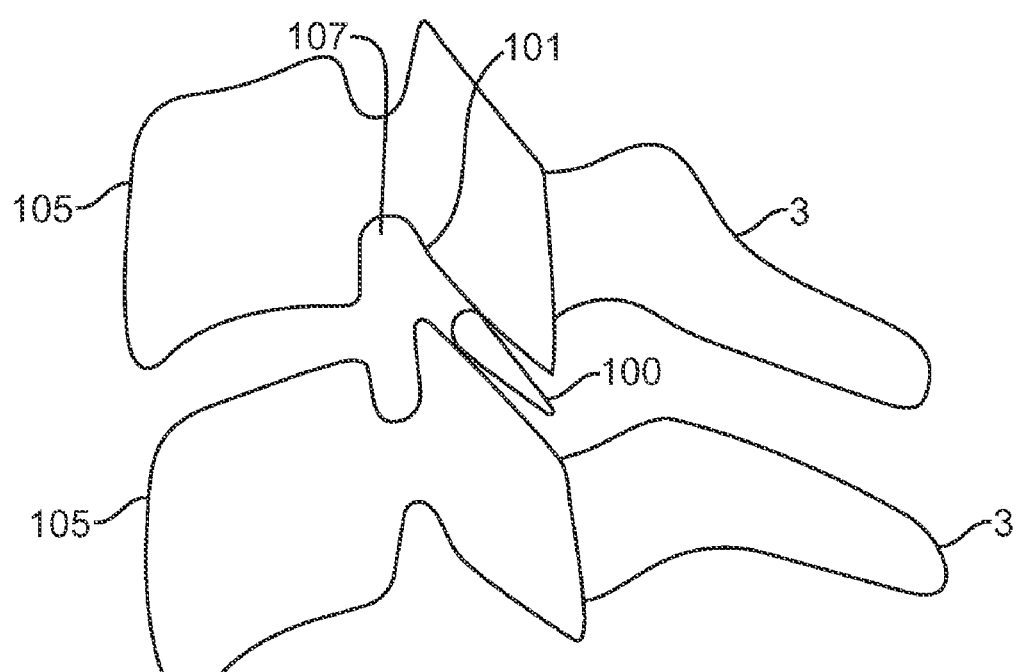
FIG. 3B depicts correction of cervical kyphosis or loss of lordosis with a wedge-shaped embodiment of the invention with the wedge positioned in the opposite direction as that depicted in FIG. 3A.

FIG. 3A shows a first embodiment 100 of the present invention, which is meant to distract at least one facet joint, in order to increase the dimension of the neural foramen while retaining facet joint mobility. The wedge-shaped embodiment or inter-facet spacer 100 is a wedge-shaped implant that can be positioned in the cervical facet joint 101 to distract the joint and reverse narrowing of the nerve root canal 107. In this embodiment or inter-facet spacer 100, the implant is positioned with the narrow portion of the wedge facing anteriorly. However, it is also within the scope of the present invention to position embodiment or inter-facet spacer 100 (FIG. 3B) with the wide portion of the wedge facing anteriorly, to correct for cervical kyphosis or loss of cervical lordosis.

It is to be understood that implants in accordance with the present invention, and/or portions thereof can be fabricated from somewhat flexible and/or deflectable material. In these embodiments, the implant and/or portions thereof can be made out of a polymer, such as a thermoplastic. For example, in one embodiment, the implant can be made from polyketone, known as polyetheretherketone ("PEEK"). Still more specifically, the implant can be made from PEEK 450G, which is an unfilled PEEK approved for medical implantation available from Victrex of Lancashire, Great Britain. Other sources of this material include Gharda located in Panoli, India. PEEK has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

The material specified has appropriate physical and mechanical properties and is suitable for carrying and spreading a physical load between the adjacent spinous processes. The implant and/or portions thereof can be formed by extrusion, injection, compression molding and/or machining techniques.

In some embodiments, the implant can comprise, at least in part, titanium or stainless steel, or other suitable implant material which is radiopaque, and at least in part a radiolucent material that does not show up under x-ray or other type of imaging. The physician can have a less obstructed view of the spine under imaging, than with an implant comprising radiopaque materials entirely. However, the implant need not comprise any radiolucent materials.

It should be noted that the material selected also can be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that unfilled PEEK. The resulting product is known to be ideal for improved strength, stiffness, or stability. Carbon-filled PEEK is known to enhance the compressive strength and stiffness of PEEK and to decrease its expansion rate. Carbon-filled PEEK offers wear resistance and load-carrying capability.

In this embodiment or inter-facet spacer 100, the implant is manufactured from PEEK, available from Victrex. As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. The spacer also can be comprised of polyetherketoneketone ("PEKK"). Other material that can be used include polyetherketone ("PEK"), polyetherketoneetherketoneketone ("PEKEKK"), and polyetheretherketoneketone ("PEEKK"), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials"; PCT Publication WO 02/00275 A1, dated Jan. 3, 2002, entitled "Bio-Compatible Polymeric Materials; and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Figure 4:
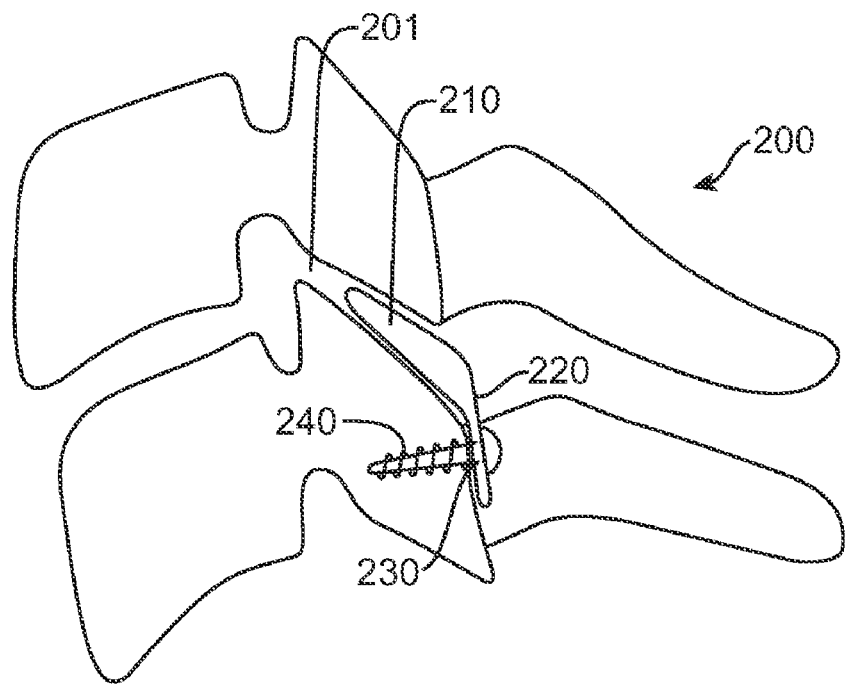
FIG. 4 shows correction of cervical stenosis or other ailment with a further embodiment of the implant of the invention including a screw fixation device for attaching to a single vertebra.

Turning now to FIG. 4, the embodiment 200 of the implant has a joint insert or inter-facet spacer 210, also herein referred to as an artificial facet joint spacer or inter-facet spacer, that is positioned in the cervical facet joint 101. The joint insert or inter-facet spacer 210 can be wedge-shaped with the narrow part of the wedge facing anteriorly. Alternatively, the joint insert or inter-facet spacer 210 need not be wedge-shaped but can be of substantially uniform thickness, the thickness determined by an individual patient's need for distraction of the cervical facet joint 201. As with embodiment 100, one objective of this embodiment is facet joint distraction, and joint mobility after implantation. The joint insert or inter-facet spacer 210 is continuous with a posterior sheath 220 bent at an angle from the joint insert or inter-facet spacer 210 to align substantially parallel with the bone. The posterior sheath can lie against the lamina, preferably against the lateral mass. The posterior sheath 220 can have a bore 230 which can accept a bone screw 240. Alternatively, the bore 230 can accept any other appropriate and/or equivalent fixation device capable of fixing the embodiment 200 to the spine. The device is thereby affixed to the vertebra, preferably by fixing to the lateral mass.

Figure 5:
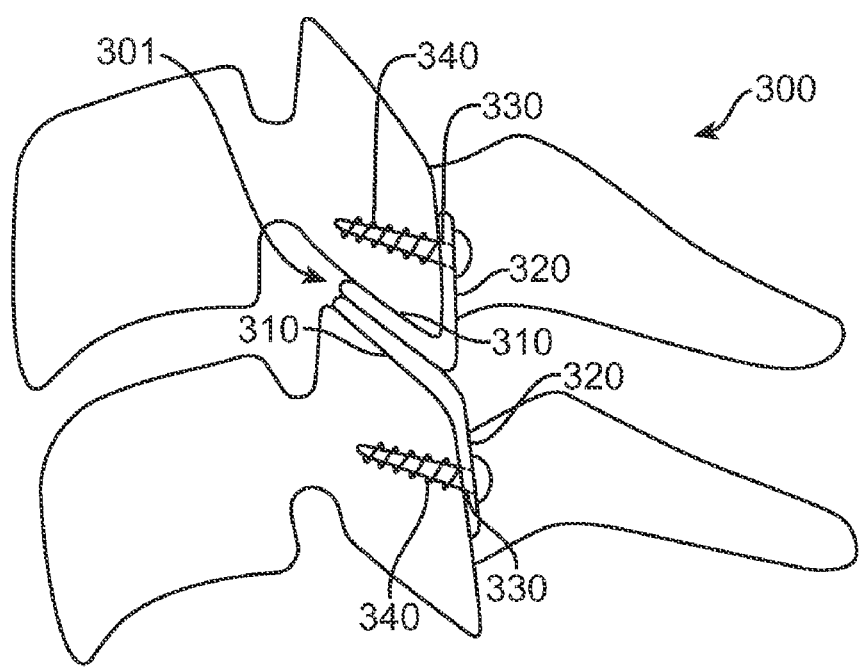
FIG. 5 shows correction of cervical stenosis or other ailment with a further embodiment of the implant of the invention, comprising screw fixation of two implants, one implant fixed to each of two adjacent vertebrae.

FIG. 5 shows embodiment 300, which is the use of two embodiments 200, each fixed to one of two adjacent cervical vertebrae. As with embodiment 200, the implanted facet joint is distracted and joint mobility is retained. A joint insert or inter-facet spacer 310 from each of the two implants is inserted and positioned in the cervical facet joint 301. In this embodiment, the joint inserts or inter-facet spacers 310 are substantially flat and parallel to each other and are not wedge-shaped. Alternatively, the joint inserts or inter-facet spacers 310 can together define a wedge-shaped insert that is appropriate for the patient. The two joint inserts or inter-facet spacers 310 combined can have, by way of example, the shape of the joint insert or inter-facet spacer 210 in FIG. 4. Embodiment 300 then can be fixed to the spine with a screw 340 or any other appropriate fixation device, inserted through a bore 330 in the posterior sheath 320. The posterior sheath 320 can be threaded to accept a screw. The screw can be embedded in the lamina, preferably in the lateral mass, where possible.

Figure 6:
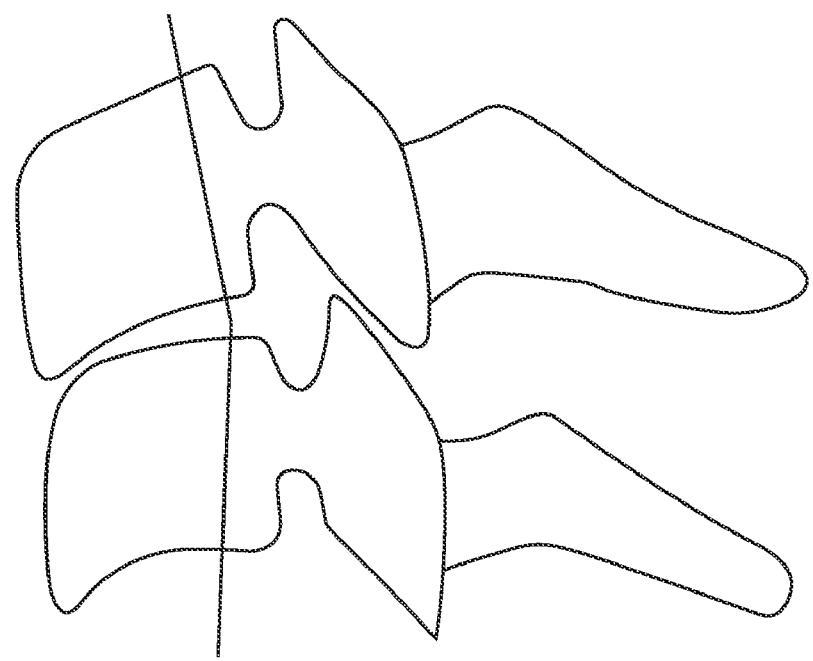
FIG. 6 shows cervical spine kyphosis, or loss of lordosis.
Figure 7:
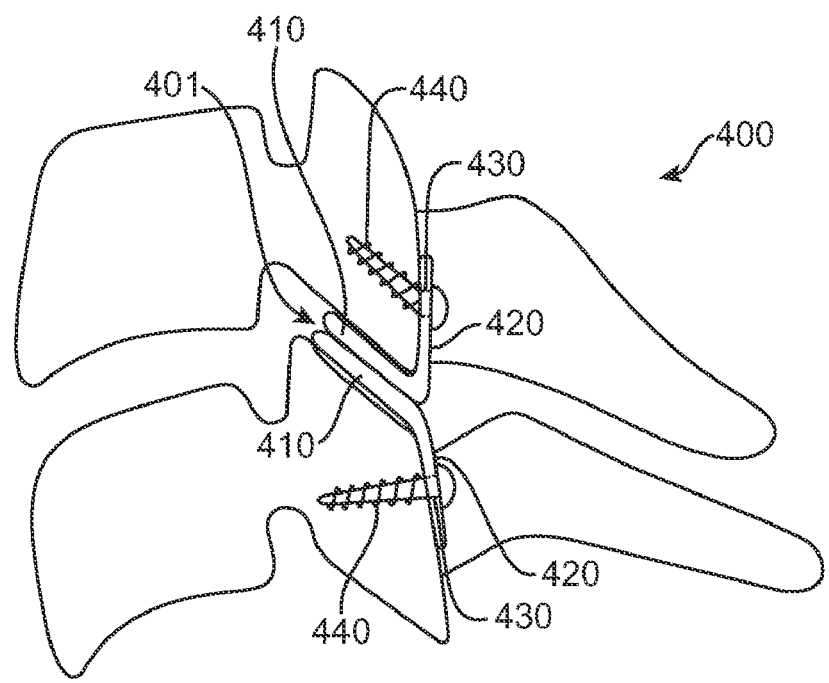
FIG. 7 shows correction of cervical kyphosis, or loss of lordosis, with a further embodiment of the implant of the invention comprising two facet implants with screw fixation.

It is within the scope of the present invention to use and/or modify the implants of the invention to correct cervical spine kyphosis, or loss of lordosis. FIG. 6 depicts a cervical spine lordosis. FIG. 7 demonstrates an embodiment 400 which contemplates positioning two implants to correct for this spinal abnormality while retaining facet joint mobility. The joint insert or inter-facet spacer 410 of each implant is shaped so that it is thicker at its anterior portion. Alternatively, the implants can be shaped to be thicker at the posterior ends, for example as depicted in FIG. 3A. The posterior sheath 420 of each implant is bent at an angle from the joint insert or inter-facet spacer 410 to be positioned adjacent to the lateral mass and/or lamina, and has a bore 430 to accept a screw 440 or other appropriate and/or equivalent fixation means to fix the embodiment 400 to the spine, preferably to the lateral mass. The placement of two joint inserts or inter-facet spacers 410 in the cervical facet joint 401 distracts the facet joint, which shifts and maintains the vertebrae into a more anatomical position to preserve the physiology of the spine.

Figure 8:
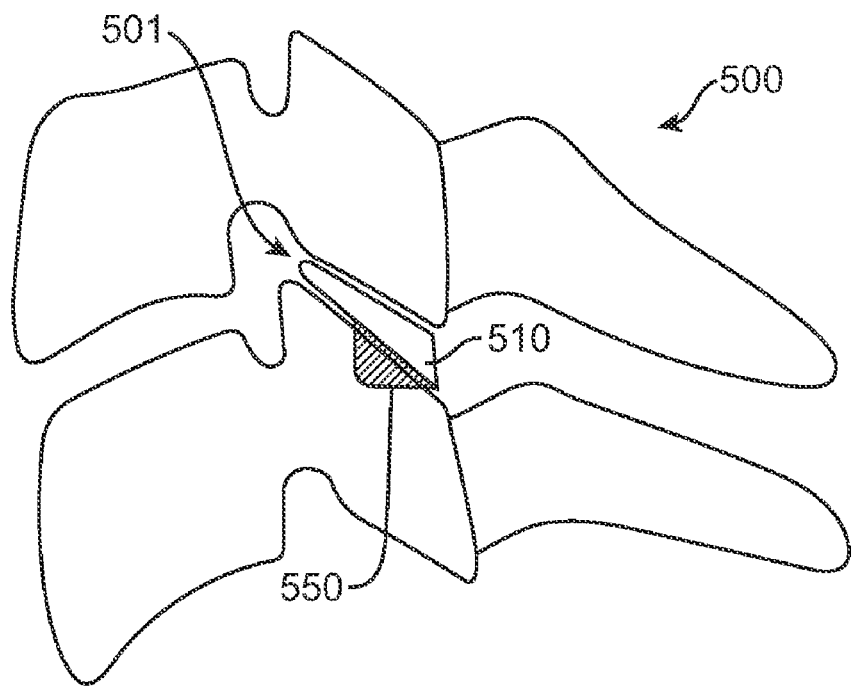
FIG. 8 shows correction of cervical stenosis or other ailment with a further embodiment of the implant of the invention, comprising a facet implant and a keel.

FIG. 8 shows a further embodiment 500 of the implant of the invention, wherein the joint insert or inter-facet spacer 510 has a keel 550 on an underside of the joint insert or inter-facet spacer 510. The keel 550 can be made of the same material or materials set forth above. The surfaces of the keel 550 can be roughened in order to promote bone ingrowth to stabilize and fix the implant 500. In other embodiments, the keel 550 can be coated with materials that promote bone growth such as, for example, bone morphogenic protein ("BMP"), or structural materials such as hyaluronic acid "HA," or other substances which promote growth of bone relative to and into the keel 550.

The keel 550 can be embedded in the facet bone, to facilitate implant retention. The keel 550 can be placed into a channel in the facet bone. The channel can be pre-cut. Teeth (not shown), preferably positioned posteriorly, also may be formed on the keel 550 for facilitating retention of the implant 500 in the cervical facet joint 501. As noted above, the joint insert or inter-facet spacer 510 can be substantially flat or wedge-shaped, depending upon the type of distraction needed, i.e., whether distraction is also necessary to correct abnormal curvature or lack of curvature in the cervical spine. Because the joint is not fused, mobility is retained, as with the embodiments described above and herein below.

Figure 9:
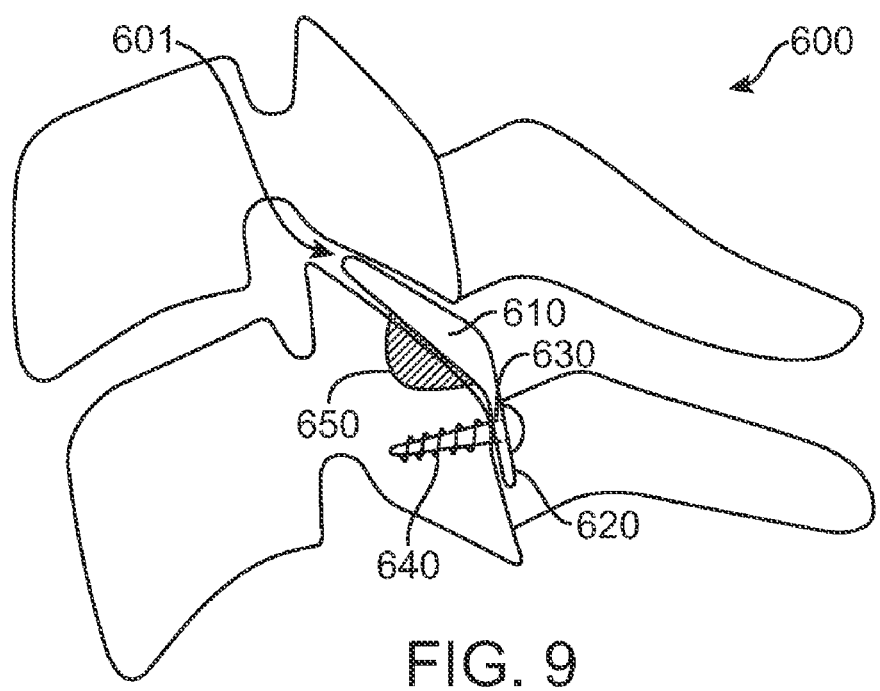
FIG. 9 shows correction of cervical stenosis or other ailment with a further embodiment of the implant of the invention, comprising facet implant, a keel, and screw fixation.

FIG. 9 illustrates that a further embodiment 600 of the implant of the invention can have both screw fixation and a keel 650 for stability and retention of the implant 600. On embodiment 600, the joint insert or inter-facet spacer 610 is continuous with a posterior sheath 620 having a bore hole 630 to accept a screw 640 which passes through the bore 630 and into the bone of the vertebrae, preferably into the lateral mass, or the lamina. The bore 630 can be threaded or not threaded where it is to accept a threaded screw or equivalent device. Alternatively, the bore 630 need not be threaded to accept a non-threaded equivalent device. The keel 650 is connected with the joint insert or inter-facet spacer 610 and embeds in the bone of the cervical facet joint 601 to promote implant retention.

Figure 10:
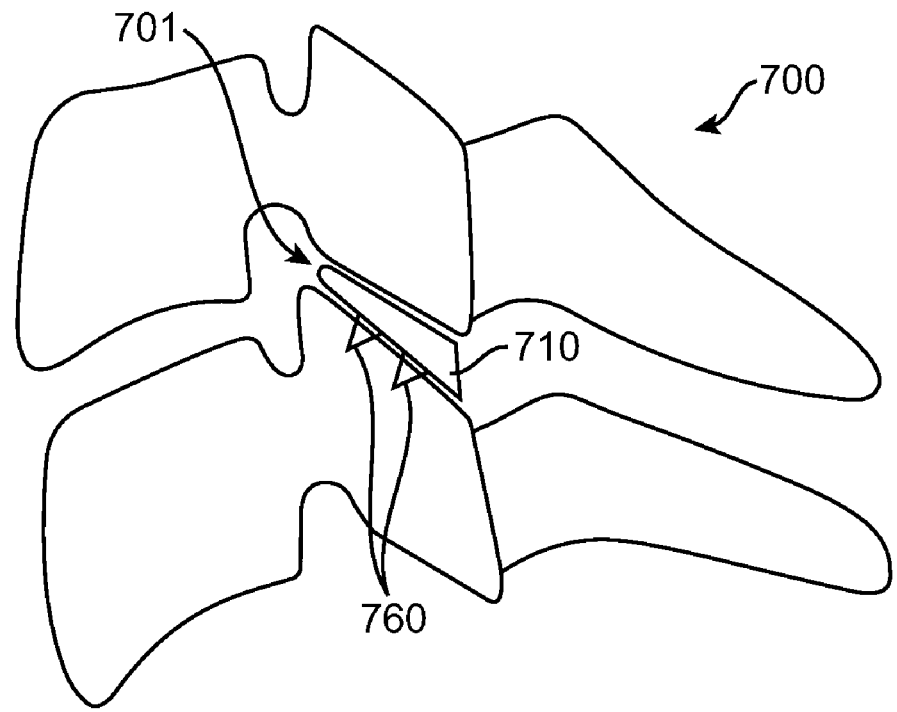
FIG. 10 shows correction of cervical stenosis or other ailment with a further embodiment of the implant of the invention, comprising a facet implant with teeth.

A further alternative embodiment 700 is illustrated in FIG. 10. In this embodiment 700, the joint insert or inter-facet spacer 710 has on a lower side at least one tooth 760. It should be clear to one of ordinary skill in the art that a plurality of teeth 760 is preferable. The teeth 760 are able to embed in the bone of the cervical facet joint 701 to facilitate retention of the implant 700 in the joint 701. The teeth 760 can face in a direction substantially opposite the direction of insertion, for retention of the implant 700. As above, the joint insert or inter-facet spacer 710 can be wedge-shaped or substantially even in thickness, depending upon the desired distraction. Because the implant distracts and is retained without fusion, facet joint mobility is retained.

Figure 11:
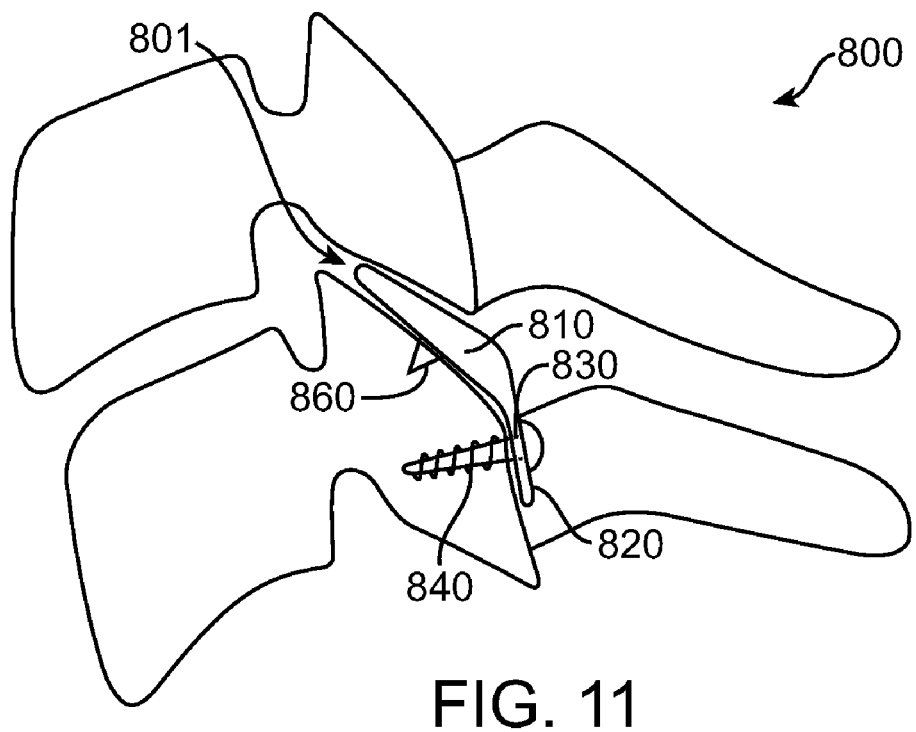
FIG. 11 depicts correction of cervical stenosis or other ailment with a further embodiment of the implant of the invention, comprising a facet implant with teeth and screw fixation.

FIG. 11 depicts a further embodiment 800 of the implant of the invention. In this embodiment 800, the joint insert or inter-facet spacer 810 is continuous with a posterior sheath 820 having a bore 830 for accepting a fixation device 840, as described above. The fixation device 840 can be a screw which fits into a threaded bore 830; alternatively, the fixation device 830 can be any other compatible and appropriate device. This embodiment 800 further combines at least one tooth 860 on an underside of the joint insert or inter-facet spacer 810 with the posterior sheath 820, bore 830 and fixation device 840 to address fixation of the implant 800 in a cervical facet joint 801. It will be recognized by one of ordinary skill in the art that the implant 800 can have a plurality of teeth 860 on the underside of the joint insert or inter-facet spacer 810.

Figure 12:
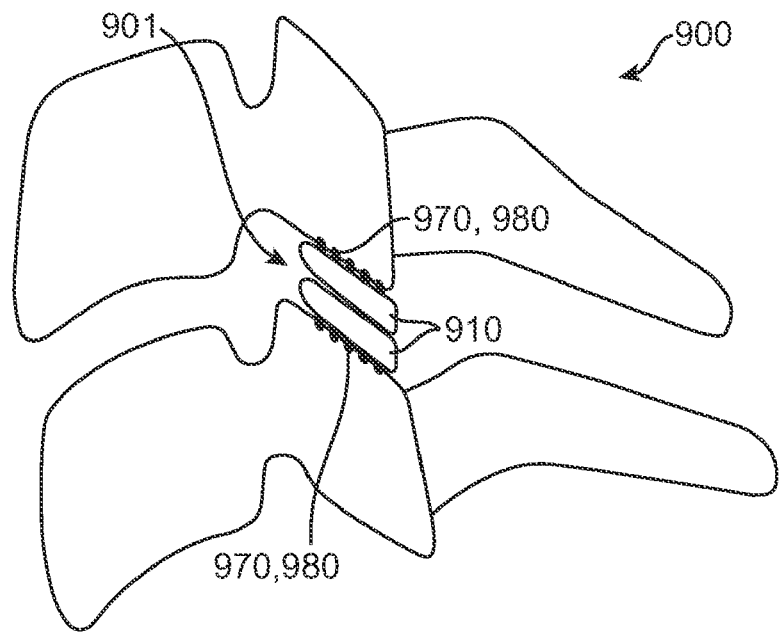
FIG. 12 depicts correction of cervical stenosis or other ailment with a further embodiment of the implant of the invention, comprising two facet implants having bony ingrowth surfaces.

FIG. 12 shows yet another embodiment 900 of an implant of the present invention. In this embodiment 900, the joint inserts or inter-facet spacers 910 of two implants 900 are positioned in a cervical facet joint 901. As described above, the joint inserts or inter-facet spacers 910 can be wedge-shaped as needed to restore anatomical curvature of the cervical spine and to distract, or the joint inserts or inter-facet spacers 910 can be of substantially uniform thickness. The implants 900 each comprise a joint insert or inter-facet spacer 910 with an outer surface 970 that interacts with the bone of the cervical facet joint 901. On the upper implant 900, the surface 970 that interacts with the bone is the upper surface 970 and on the lower implant 900, the surface 970 that interacts with the bone is the lower surface 970. Each surface 970 can comprise a bone ingrowth surface 980 to create a porous surface and thereby promote bone ingrowth and fixation. One such treatment can be with plasma spray titanium, and another, with a coating of sintered beads. Alternatively, the implant 900 can have casted porous surfaces 970, where the porous surface is integral to the implant 900. As a further alternative, the surfaces 970 can be roughened in order to promote bone ingrowth into these defined surfaces of the implants 900. In other embodiments, the surfaces 970 can be coated with materials that promote bone growth such as for example bone morphogenic protein ("BMP"), or structural materials such as hyaluronic acid ("HA"), or other substances which promote growth of bone on other external surfaces 970 of the implant 900. These measures facilitate fixation of the implants 900 in the facet joint, but do not result in fusion of the joint, thereby retaining facet joint mobility, while also accomplishing distraction of the joint.

Figure 13:
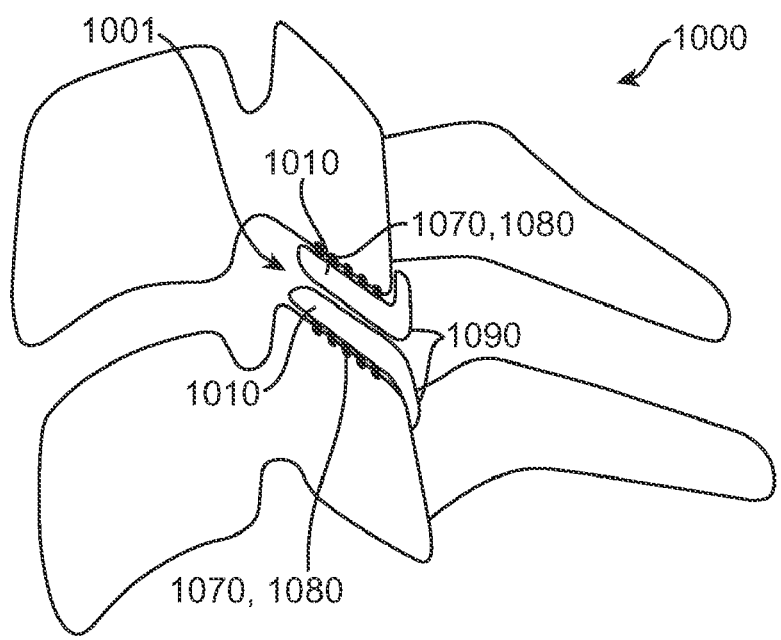
FIG. 13 depicts correction of cervical stenosis or other ailment with a further embodiment of the implant of the invention, comprising two facet implants having bony ingrowth surfaces and posterior alignment guide.

FIG. 13 depicts yet another embodiment 1000 of the implant of the present invention. In this embodiment 1000, the joint inserts or inter-facet spacers 1010 of two implants 1000 are positioned in a cervical facet joint 1001. As described above, the joint inserts or inter-facet spacers 1010 can be wedge-shaped as needed to restore anatomical curvature of the cervical spine and to distract, or the joint inserts or inter-facet spacers 1010 can be of substantially uniform thickness. The implants 1000 each comprise a joint insert or inter-facet spacer 1010 with an outer surface 1070 that interacts with the bone of the cervical facet joint 1001. On the upper implant 1000, the surface 1070 that interacts with the bone is the upper surface and on the lower implant 1000, the surface 1070 that interacts with the bone is the lower surface. As set forth above, each outer surface 1070 can comprise a bone ingrowth surface 1080 to create a porous surface and thereby promote bone ingrowth and fixation, without facet joint fusion and loss of mobility. In one preferred embodiment, the bone ingrowth surface 1080 can be created with plasma spray titanium, and/or with a coating of sintered beads. In an alternative preferred embodiment, the implant 1000 can have casted porous surfaces 1070, where the porous surface is integral to the implant 1000. In a further alternative preferred embodiment, the surfaces 1070 can be roughened in order to promote bone ingrowth into these defined surfaces of the implants 1000. In other preferred embodiments, the surfaces 1070 can be coated with materials that promote bone growth such as for example BMP, or structural materials such as HA, or other substances which promote growth of bone on other external surfaces 1070 of the implant 1000.

The implant 1000 can have a posterior alignment guide 1090. The posterior alignment guides 1090 of each implant 1000 can be continuous with the joint inserts or inter-facet spacers 1010. The posterior alignment guides substantially conform to the bone of the vertebrae when the joint inserts or inter-facet spacers 1010 are inserted into the cervical facet joint 1001. The posterior alignment guides 1090 are used to align the implants 1000 so that the joint inserts or inter-facet spacers 1010 contact each other and not the bones of the cervical facet joint 1001 when the joint inserts or inter-facet spacers 1010 are positioned in the cervical facet joint 1001.

Figure 14:
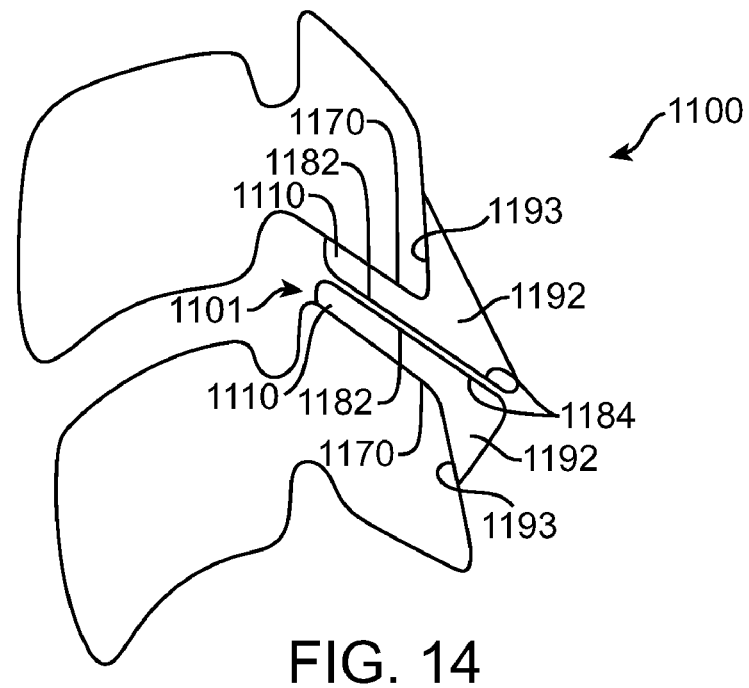
FIG. 14 shows correction of cervical stenosis or other ailment with a further embodiment of the implant of the invention, comprising two facet implants with increased facet joint contact surfaces.

FIG. 14 depicts a further embodiment 1100 of the implant of the present invention. In this embodiment 1100, the joint inserts or inter-facet spacers 1110 of two implants 1100 are inserted into the cervical facet joint 1101. Each of the joint inserts or inter-facet spacers 1110 is continuous with a cervical facet joint extender or facet-extending surface 1192. The bone contacting surfaces 1170 of the joint inserts or inter-facet spacers 1110 are continuous with, and at an angle to, the bone contacting surfaces 1193 of the cervical facet joint extenders 1192, so that the cervical facet joint extenders 1192 conform to the bones of the vertebrae exterior to the cervical facet joint 1101. The conformity of the cervical facet joint extenders 1192 is achieved for example by forming the cervical facet joint extenders 1192 so that when the join inserts or inter-facet spacers 1110 are positioned, the cervical facet joint extenders 1192 curve around the bone outsider the cervical facet joint 1101.

The cervical facet joint extenders have a second surface 1184 that is continuous with the joint articular surfaces 1182 of the joint inserts or inter-facet spacers 1110. The second surfaces 1184 extend the implant 1100 posteriorly to expand the joint articular surfaces 1182 and thereby to increase contact and stability of the spine at least in the region of the implants 1100. It is to be understood that such facet joint extenders 1192 can be added to the other embodiments of the invention described and depicted herein.

Figure 15:
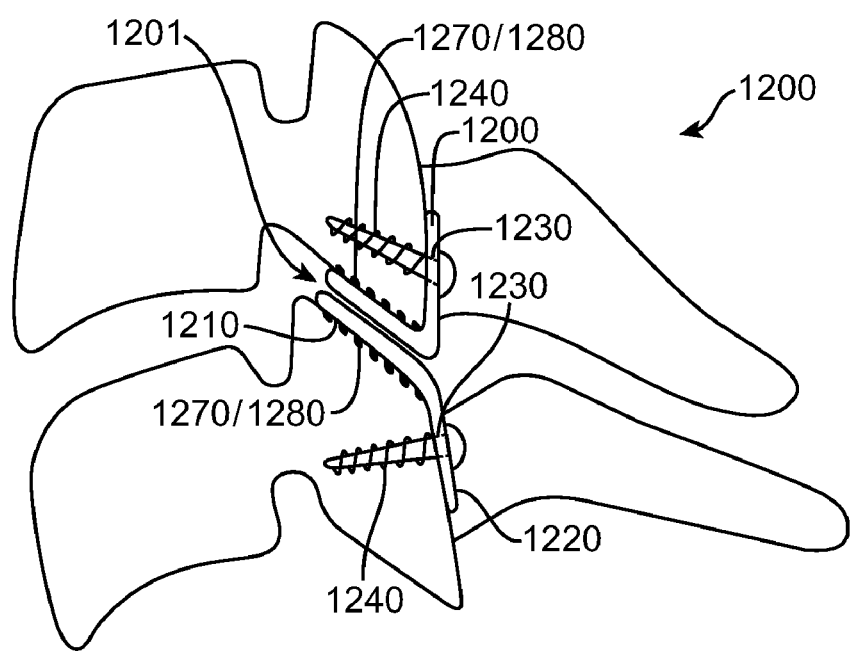
FIG. 15 shows correction of cervical stenosis or other ailment with a further embodiment of the implant of the invention, comprising two facet implants having bony ingrowth surfaces and screw fixation.

The embodiment depicted in FIG. 15 shows two implants 1200 positioned in a cervical facet joint 1201, having bony ingrowth surfaces as one preferred method of fixation, and using screws as another preferred method of fixation. In this embodiment, each of two implants 1200 has a joint insert or inter-facet spacer 1210 positioned in a cervical facet joint 1201. As described above, the joint inserts or inter-facet spacers 1210 can be wedge-shaped as needed to restore anatomical curvature of the cervical spine and to distract, or the joint inserts or inter-facet spacers 1210 can be of substantially uniform thickness. The implants 1200 each comprise a joint insert or inter-facet spacers 1210 with an outer surface 1270 that interacts with the bone of the cervical facet joint 1001. On the upper implant 1200, the surface 1270 that interacts with the bone is the upper surface and on the lower implant 1200, the surface 1270 that interacts with the bone is the lower surface. As set forth above, each outer surface 1270 can comprise a bone ingrowth surface 1280 to create a porous surface and thereby promote bone ingrowth and fixation. In one preferred embodiment, the bone ingrowth surface 1280 can be created with plasma spray titanium, and/or with a coating of sintered beads. In an alternative preferred embodiment, the implant 1200 can have casted porous surfaces 1270, where the porous surface is integral to the implant 1200. In a further alternative embodiment, the surfaces 1270 can be roughened in order to promote bone ingrowth into these defined surfaces of the implants 1200. In other preferred embodiments, the surfaces 1270 can be coated with materials that promote bone growth such as for example BMP, or structural materials such as HA, or other substances which promote growth of bone on other external surfaces 1270 of the implant 1200.

Screw fixation or other appropriate fixation also can be used with implants 1200 for fixation in the cervical facet joint 1201. The joint insert or inter-facet spacer 1210 is continuous with a posterior sheath 1220 bent at an angle from the joint insert or inter-facet spacer 1210 to align substantially parallel with the bone, preferably the lateral mass or lamina. The posterior sheath 1220 can have a bore 1230 which can accept a bone screw 1240, preferably into the lateral mass or lamina. Alternatively, the bore 1230 can accept any other appropriate and/or equivalent fixation means for fixing the embodiment 1200 to the spine.

Figure 16:
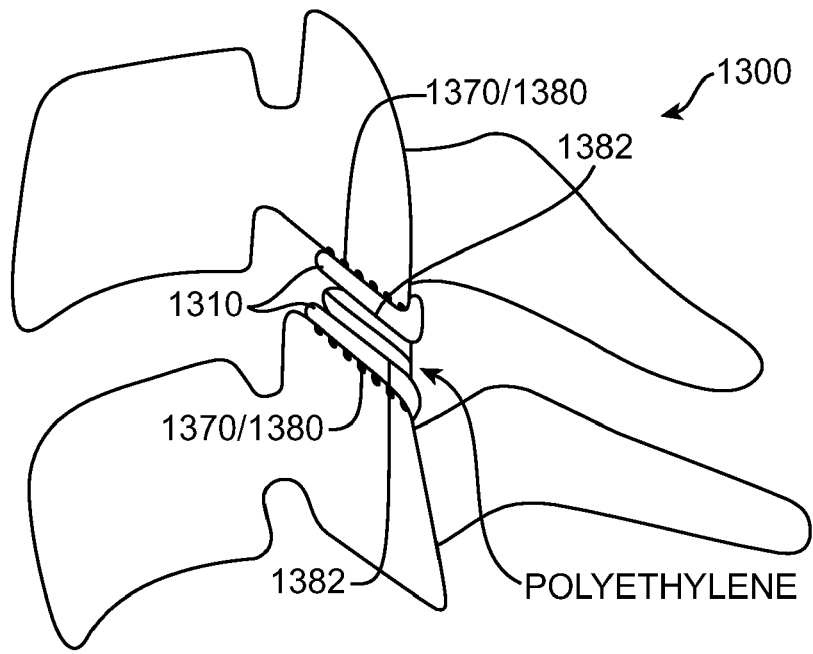
FIG. 16 shows correction of cervical stenosis or other ailment with a further embodiment of the implant of the invention, comprising two facet implants with articular inner surfaces.

FIG. 16 depicts a further preferred embodiment of the present invention. In this embodiment 1300, two joint inserts or inter-facet spacers 1310 are positioned in the cervical facet joint 1301. The joint inserts or inter-facet spacers each have outer surfaces 1370 that interact with the bone of the vertebrae forming the cervical facet joint. These outer surfaces 1370 of the embodiment 1300 can be treated to become bone ingrowth surfaces 1380, which bone ingrowth surfaces 1380 contribute to stabilizing the two joint inserts or inter-facet spacers 1310 of the implant 1300. In one preferred embodiment, the bone ingrowth surface 1380 can be created with plasma spray titanium, and/or with a coating of sintered beads. In an alternative preferred embodiment, the implant 1300 can have casted porous surfaces 1370, where the porous surface is integral to the implant 1300. In a further alternative embodiment, the surfaces 1370 can be roughened in order to promote bone ingrowth into these defined surfaces of the implants 1300. In other preferred embodiments, the surfaces 1370 can be coated with materials that promote bone growth such as for example BMP, or structural materials such as HA, or other substances which promote growth of bone on other external surfaces 1370 of the implant 1300. This fixation stabilizes the implant 1300 in the facet joint without fusing the joint, and thus the implant preserves joint mobility, while accomplishing distraction and increasing foraminal dimension.

Also shown in FIG. 16 are articular inner surfaces 1382 of the implants 1300. These surfaces can be formed from a metal and polyethylene, the material allowing flexibility and providing for forward bending/flexion and backward extension of the cervical spine. The embodiment 1300 of FIG. 16 can be made in at least two configurations. The first configuration includes a flexible spacer 1382 made, by way of example, using polyethylene or other suitable, flexible implant material. The flexible spacer 1382 can be permanently affixed to the upper and lower joint insert or inter-facet spacer 1310. The spacer 1382 can be flat or wedge-shaped or have any other shape that would correct the curvature of the spine. In other configurations, the spacer 1382 can be affixed to only the upper insert or inter-facet spacer 1310 or to only the lower insert or inter-facet spacer 1310. Alternatively, a spacer 1382 can be affixed to each of an upper insert or inter-facet spacer 1310 and a lower insert 1310 with the upper insert or inter-facet spacer 1310 and the lower insert or inter-facet spacer 1310 being separate units.

Figure 17:
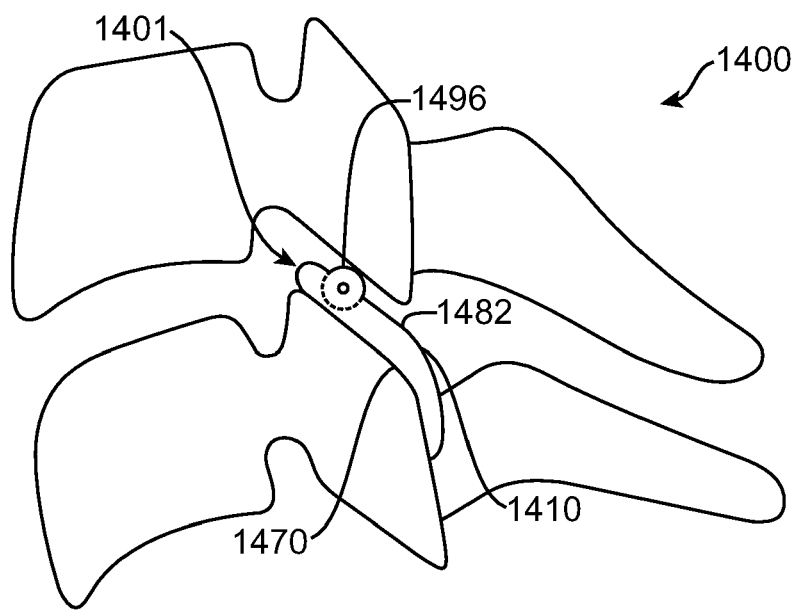
FIG. 17 shows correction of cervical stenosis or other ailment with a further embodiment of the implant of the invention, comprising a facet joint implant with a roller.
Figure 18:
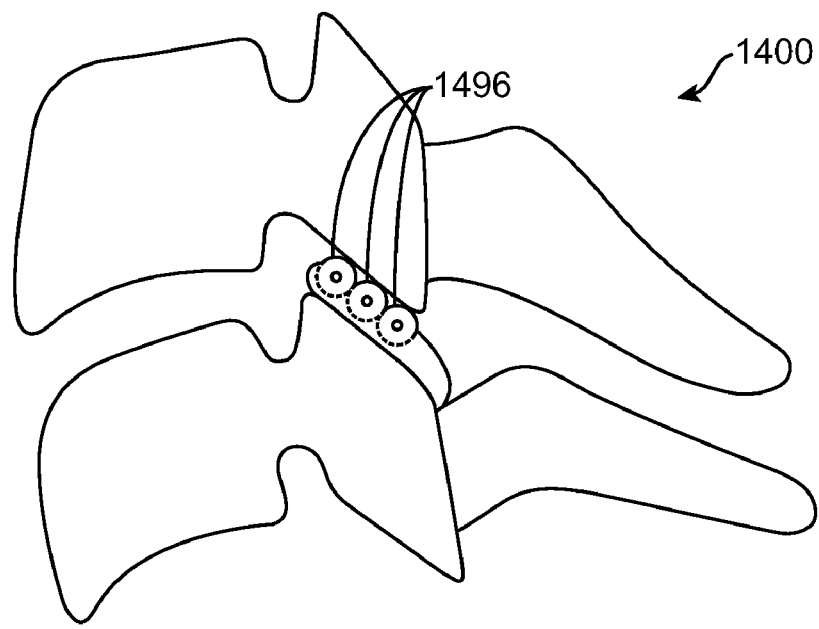
FIG. 18 shows correction of cervical stenosis or other ailment with a further embodiment of the implant of the invention, comprising a facet joint implant with a plurality of rollers.

FIG. 17 shows a further preferred embodiment of the implant of the present invention. In this embodiment 1400, the implant has a roller 1496 mounted on a joint insert or inter-facet spacer 1410, the roller being a further means of preserving joint mobility while accomplishing distraction. Both the roller 1496 and the joint insert or inter-facet spacer 1410 are positioned in the cervical facet joint 1401. The joint insert or inter-facet spacer 1410 as in other embodiments has a bone-facing surface 1470 and joint articular surface 1482. The bone-facing surface 1470 can interact with the lower bone of the cervical facet joint 1401. Alternatively, the bone-facing surface can interact with the upper bone of the cervical facet joint 1401. Between the bone-facing surface 1470 and the joint articular surface 1482 is an axis about which the roller 1496 can rotate. The roller 1496 rotates in a cavity in the joint insert or inter-facet spacer 1410, and interacts with the top bone of the cervical facet joint 1401. Alternatively, where the bone-facing surface 1470 of the joint insert or inter-facet spacer 1410 interacts with the top bone of the cervical facet joint 1401, the roller 1496 rotates in a cavity in the joint insert or inter-facet spacer 1410 and interacts with the lower bone of the cervical facet joint 1401. The rotation of the roller 1496 allows flexion and extension of the cervical spine. Alternatively, a roller such as roller 1496 can be secured to an upper and a lower insert such as inserts or inter-facet spacers 410 in FIG. 7. As depicted in FIG. 18, a plurality of rollers 1496 also is possible.

Figure 19:
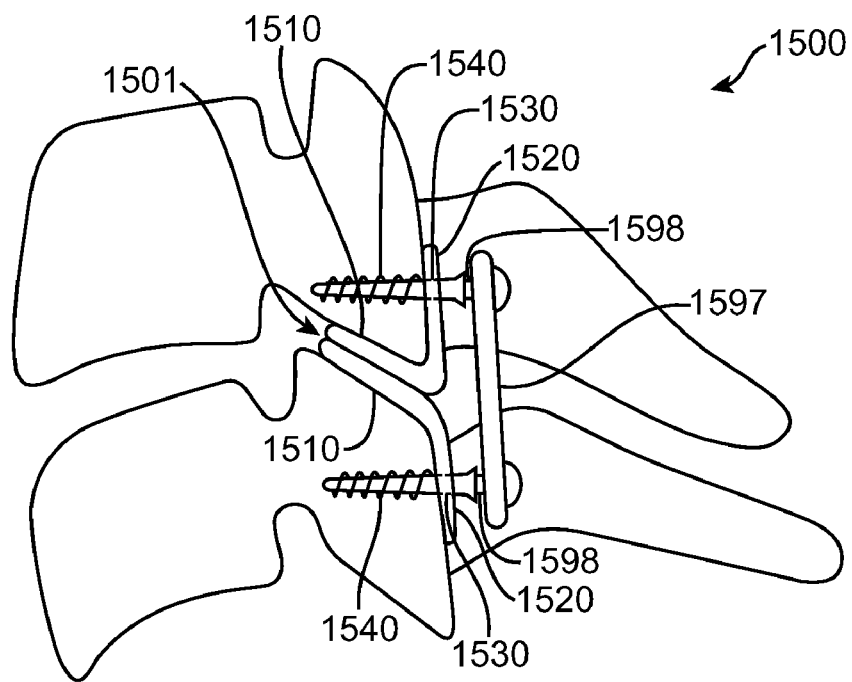
FIG. 19 shows correction of cervical stenosis or other ailment with a further embodiment of the implant of the invention, comprising two facet joint implants, screw fixation, and elastic restraint.

FIG. 19 depicts a further embodiment of the implant of the present invention. In this embodiment, two implants 1500 are implanted in the cervical facet joint 1501. Screw fixation or other appropriate fixation is used with implants 1500 for fixation in the cervical facet joint 1501. The joint insert or inter-facet spacer 1510 is continuous with a posterior sheath 1520 bent at an angle from the joint insert or inter-facet spacer 1510 to align substantially parallel with the bone, preferably the lateral mass or lamina. The posterior sheath 1520 of each implant 1500 can have a bore 1530 which can accept a bone screw 1540, preferably into the lateral mass or lamina. Alternatively, the bore 1530 can accept any other appropriate and/or equivalent fixation means for fixing the embodiment 1500 to the spine. The head of the screw 1540 in each posterior sheath 1520 of each implant 1500 has a groove 1598 or other mechanism for retaining an elastic band 1597. The elastic band 1597 is looped around each of the two screws 1540 to restrain movement of the cervical spine without eliminating facet joint mobility. The band 1597 preferably can restrain flexion and lateral movement. The elastic band 1597 can be made of a biocompatible, flexible material.

Figure 20:
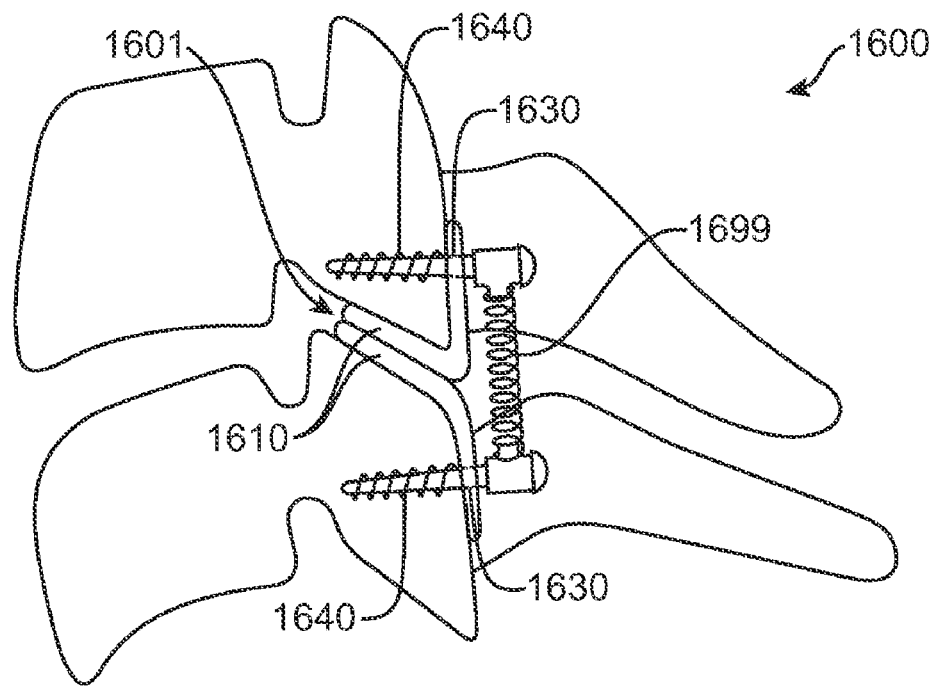
FIG. 20 shows correction of cervical stenosis or other ailment with a further embodiment of the implant of the invention, comprising two facet joint implants, screw fixation, and spring restraint.

FIG. 20 shows an alternative to use of an elastic band as in FIG. 19. In the embodiment in FIG. 20, the elastic band is replaced with a spring restraint 1699, which extends between the heads of two screws 1640, one screw fixing each of two implants 1600 in the cervical facet joint 1601.

Figure 21:
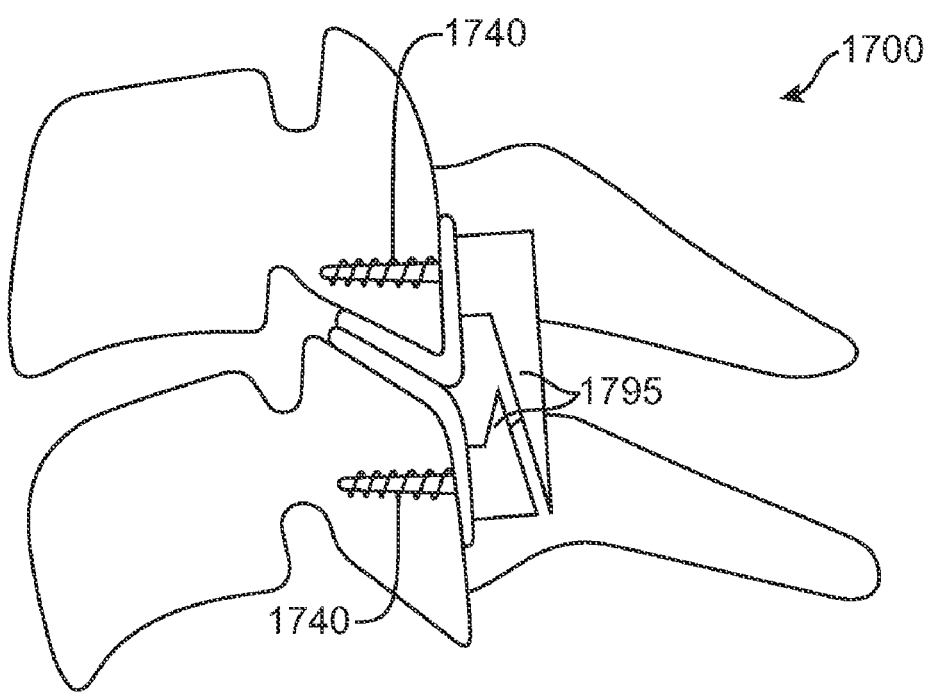
FIG. 21 shows correction of cervical stenosis or other ailment with a further embodiment of the implant of the invention, comprising two facet joint implants, screw fixation, and magnetic restraint.
Figure 22A:
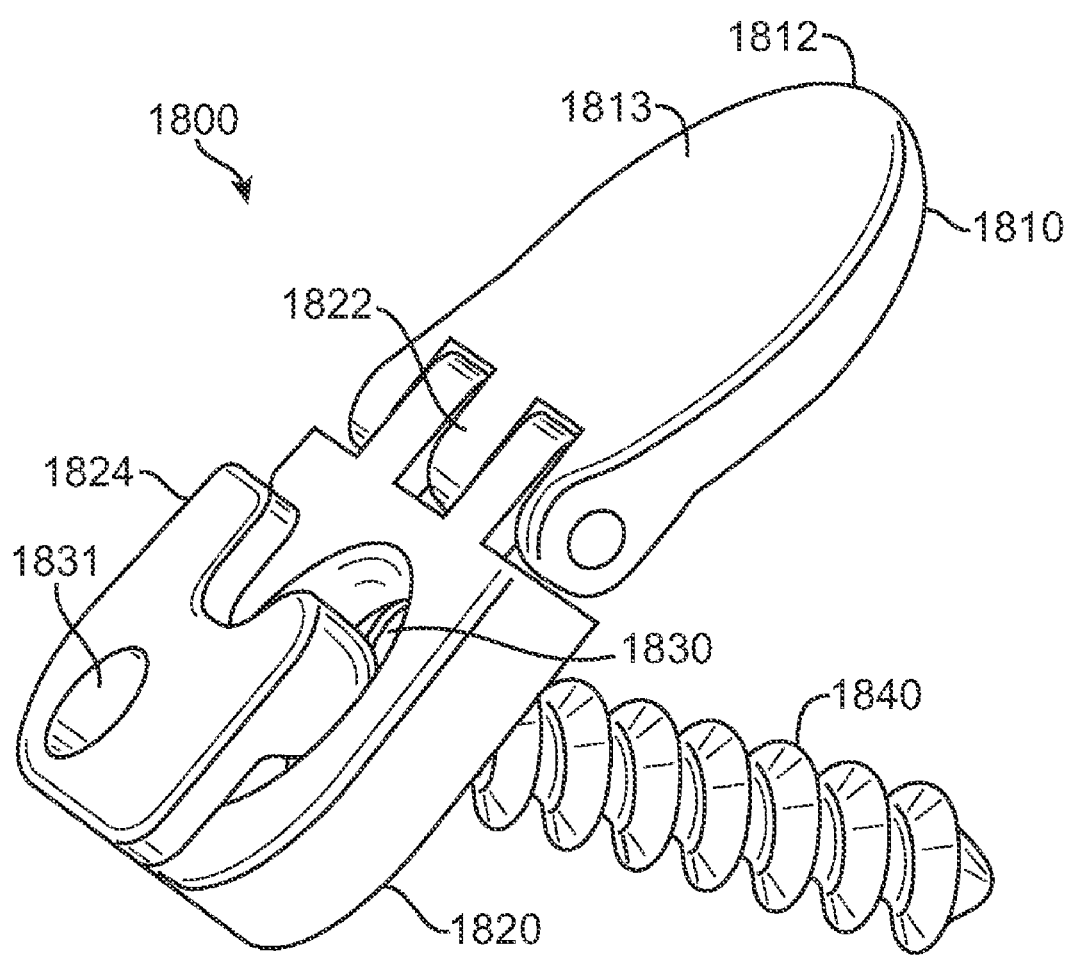
FIG. 22A shows a perspective view of a further embodiment of implant of the invention.
Figure 22B:
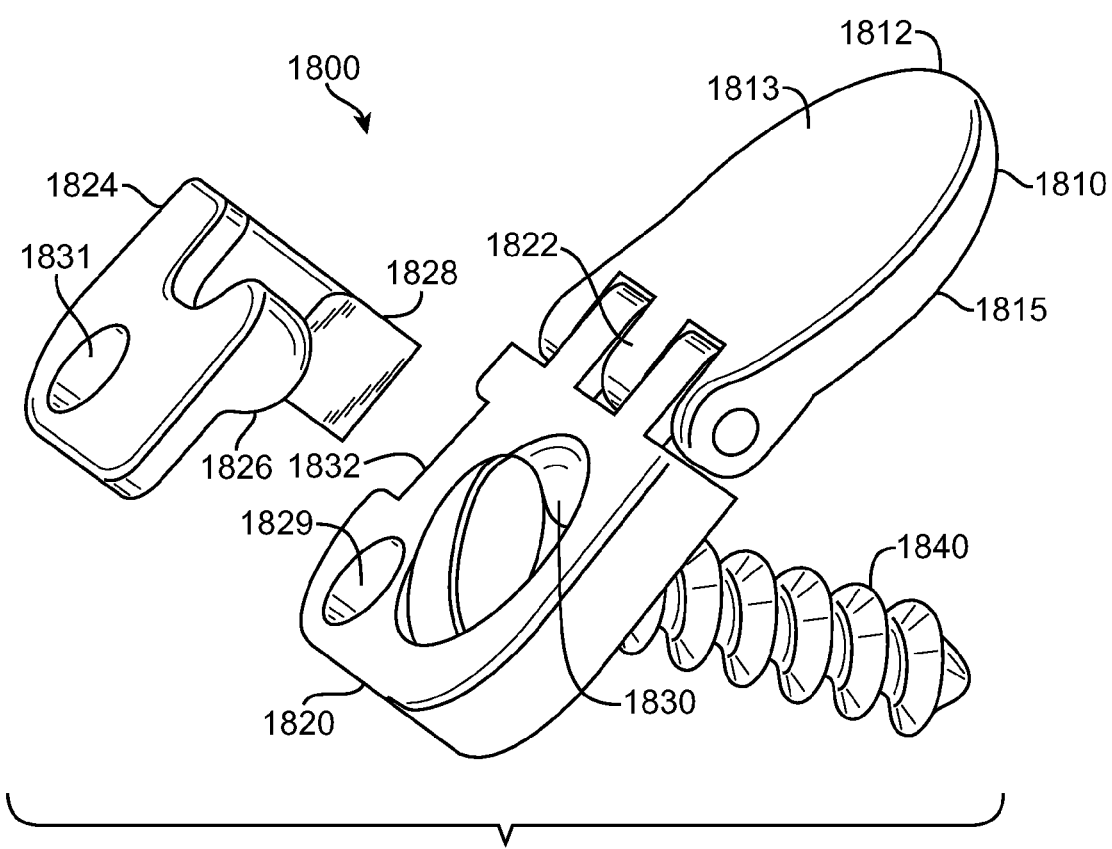
FIG. 22B shows a perspective exploded view of the embodiment of the invention shown in FIG. 22A.
Figure 23A:
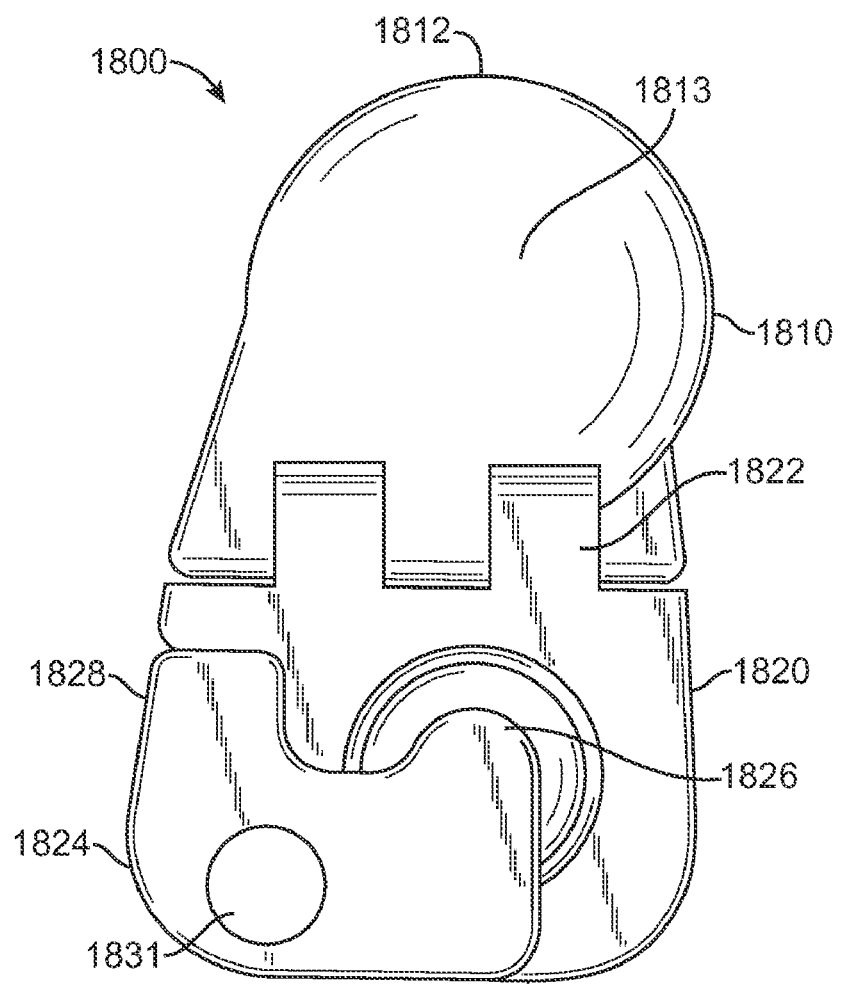
FIG. 23A depicts a posterior view of the embodiment of the implant of the invention shown in FIG. 22A.
Figure 23B:
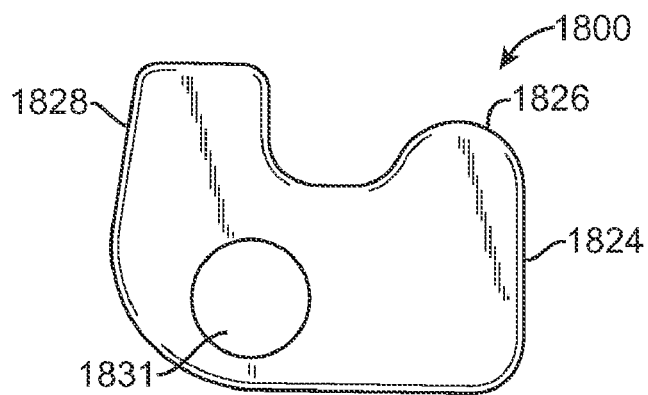
FIG. 23B shows a posterior view of a locking plate of the embodiment of the implant of the invention shown in FIG. 22A.
Figure 24A:
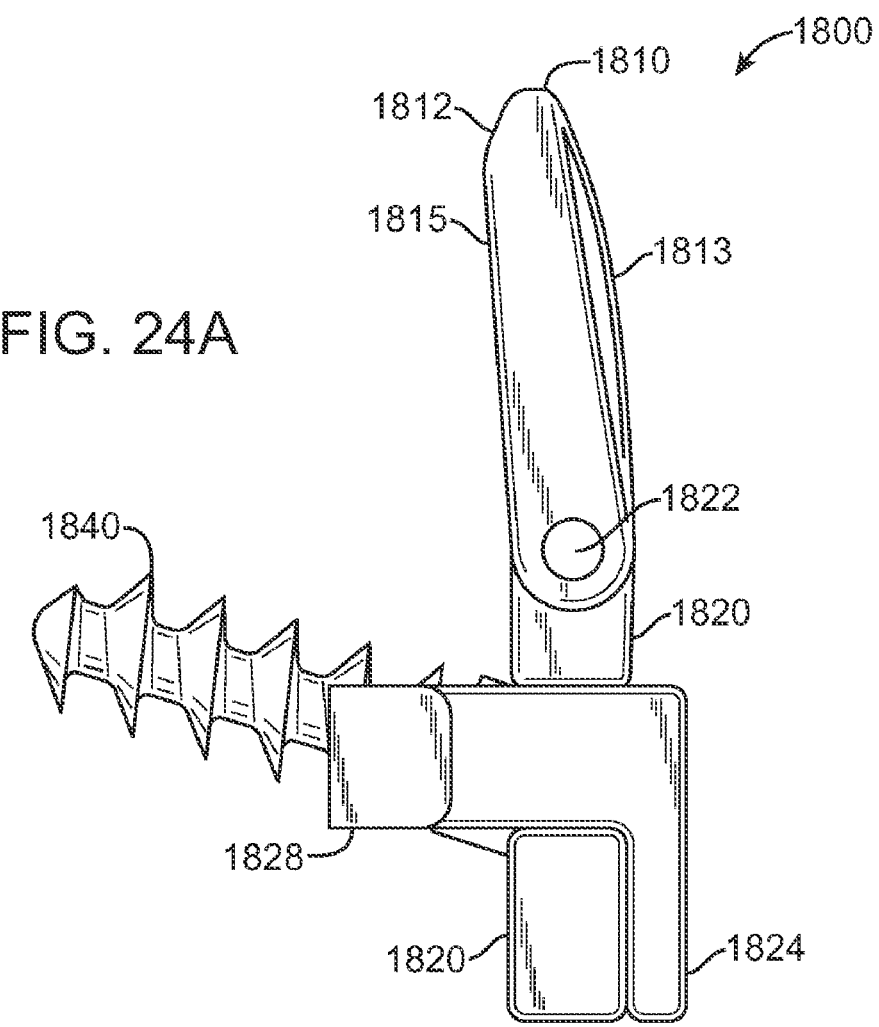
FIG. 24A depicts a lateral side view of the embodiment of the implant of the invention shown in FIG. 22A.
Figure 24B:
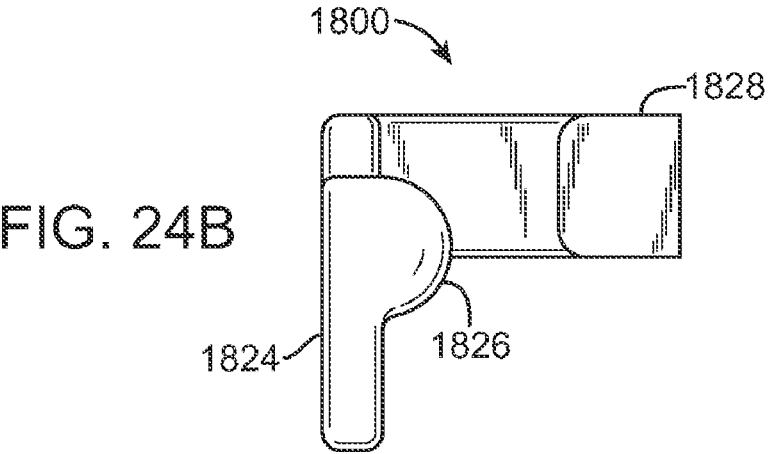
FIG. 24B shows a lateral side view of the keel of the locking plate of the embodiment of the implant of the invention shown in FIG. 22A.

FIG. 21 shows another alternative to using an elastic band and/or a spring as in FIG. 19 or 20. In FIG. 21, magnets 1795 are used for restraint between the two screws 1740. The magnet 1795 can either be comprised of two opposing magnetic fields or two of the same magnetic fields to operate to restrain movement. The head of one of the two screws 1740 is magnetized, and the head of the other screw 1740 is magnetized with either the same or opposite field. If the magnets 1795 have the same polarity, the magnets 1795 repel each other and thus limit extension. If the magnets 1795 have opposite polarities, the magnets 1795 attract each other and thus limit flexion and lateral movement.

FIGS. 22A-24B, depict a further embodiment 1800 of the implant of the present invention. In this embodiment, an artificial facet joint spacer (or insert) or inter-facet spacer (or insert) 1810 is connected with a lateral mass plate (also referred to as an anchoring plate) 1820 with a hinge 1822. The hinge 1822 allows the lateral mass plate 1820 to bend at a wide range of angles relative to the artificial facet joint spacer or inter-facet spacer and preferably at an angle of more than 90 degrees, and this flexibility facilitates positioning and insertion of the artificial facet joint spacer or inter-facet spacer 1810 into a patient's facet joint, the anatomy of which can be highly variable among individuals. This characteristic also applies to embodiments described below, which have a hinge or which are otherwise enabled to bend by some equivalent structure or material property. The hinge 1822 further facilitates customizing the anchoring of the implant, i.e., the positioning of a fixation device. The hinge enables positioning of the lateral mass plate 1820 to conform to a patient's cervical spinal anatomy, and the lateral mass plate 1820 accepts a fixation device to penetrate the bone. The artificial facet joint spacer or inter-facet spacer 1810 can be curved or rounded at a distal end 1812 (FIG. 23A), and convex or dome-shaped on a superior surface 1813 to approximate the shape of the bone inside the facet joint. The inferior surface 1815 can be flat or planar. Alternatively, the inferior surface 1815 can be concave. As another alternative, the inferior surface 1815 can be convex.

The lateral mass plate 1820, when implanted in the spine, is positioned outside the facet joint, preferably against the lateral mass or against the lamina. The lateral mass plate 1820 has a bore 1830 therethrough. The bore 1830 can accept a bone screw 1840, also referred to as a lateral mass screw, to secure the lateral mass plate 1820 preferably to the lateral mass or alternatively to another part of the spine, and thus to anchor the implant. The lateral mass screw 1840 preferably has a hexagonal head to accept an appropriately-shaped wrench. As described below, the head accepts a compatible probe 1826 from a locking plate 1824.

The locking plate 1824 includes a keel 1828 with a wedge shaped distal end to anchor the implant, preferably in the lateral mass or in the lamina, outside the facet joint and to prevent rotation of the lateral mass plate 1820 and the locking plate 1824. The keel 1828 aligns with a groove 1823 through an edge of the lateral mass plate 1820 to guide and align the keel 1828 as the keel 1828 cuts into a vertebra.

As noted above, the locking plate 1824 includes a probe 1826 that fits against the head of the lateral mass screw 1840. The locking plate further includes a bore 1831 that can accept a machine screw (not shown) which passes through to an aligned bore 1829 in the lateral mass plate 1820 to hold the locking plate 1824 and the lateral mass plate 1820 together without rotational displacement relative to each other. The locking plate 1824 thus serves at least two functions: (1) maintaining the position of the lateral mass screw 1840 with the probe 1826, so that the screw 1840 does not back out; and (2) preventing rotation of the implant with the keel 1828 and machine screw relative to the cervical vertebra or other vertebrae.

It is to be understood that other mechanisms can be used to lock the locking plate 1824 to the lateral mass plate 1820. For example, the locking plate can include a probe with barbs that can be inserted into a port in the lateral mass plate. The barbs can become engaged in ribs that define the side walls of the port in the lateral mass plate.

Figure 25A:
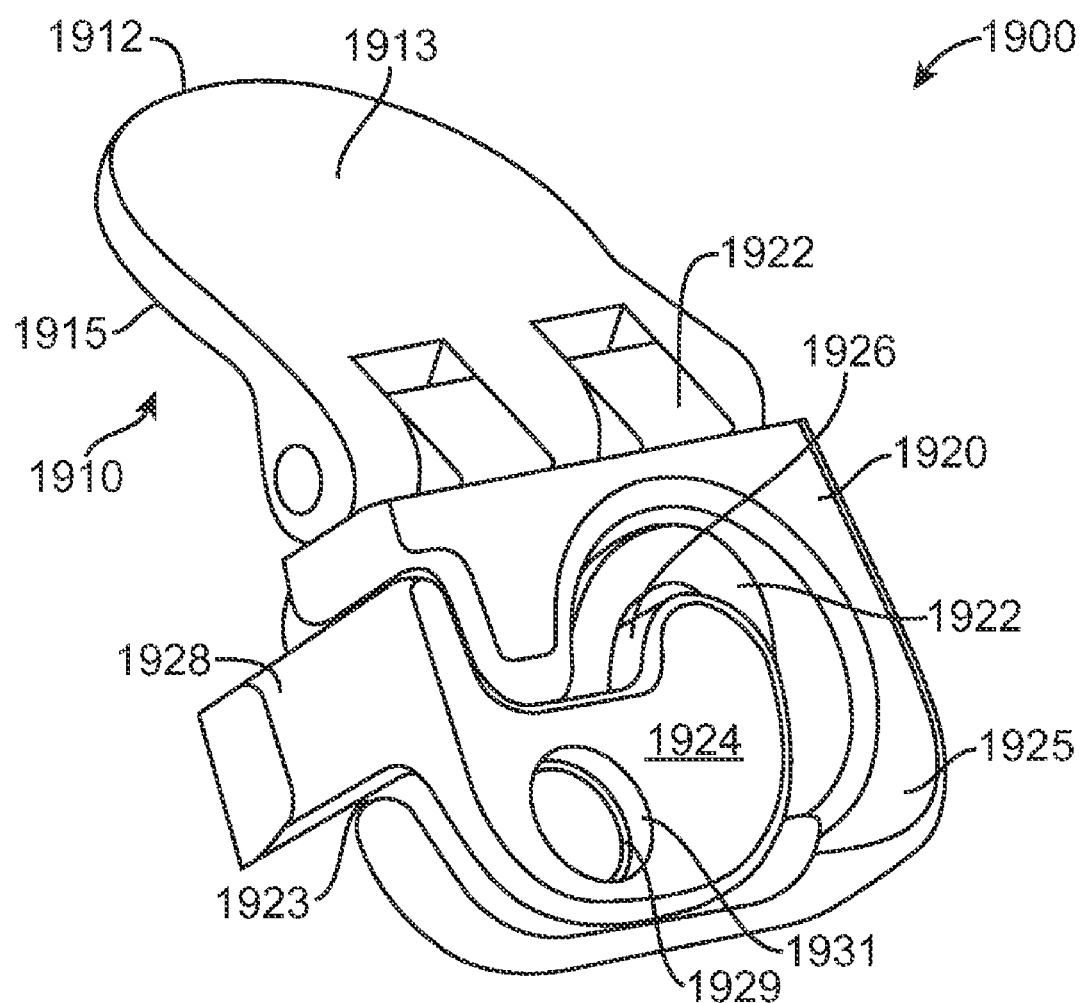
FIG. 25A shows a perspective view of a further embodiment of the implant of the invention.
Figure 25B:
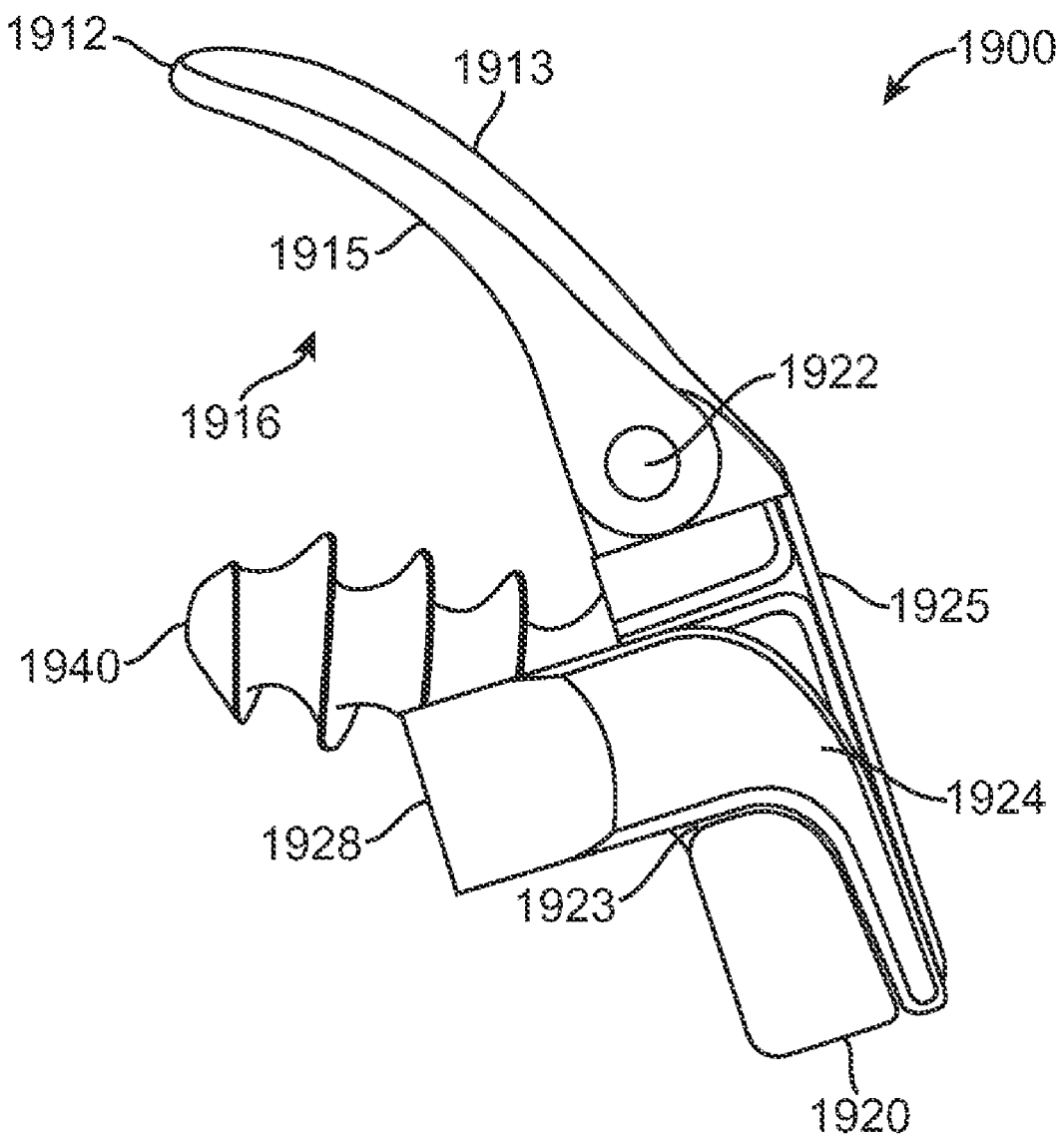
FIG. 25B shows a side view of the embodiment of the implant of the invention in FIG. 25A, having a curved, uniformly-thick artificial facet joint spacer or inter-facet spacer including a tapered end.

In the preferred embodiment depicted in FIGS. 25A, 25B, the lateral mass plate 1920 includes a recessed area 1922 for receiving the locking plate 1924 so that the locking plate 1924 is flush with the upper surface 1925 of the lateral mass plate 1920 when the probe 1926 is urged against the lateral mass screw 1940 and the keel 1928 is inserted into the lateral mass or the lamina of the vertebra. In the preferred embodiment depicted in FIGS. 25A, 25B, the shape and contours of the artificial facet joint spacer or inter-facet spacer 1910 can facilitate insertion of the artificial facet joint spacer or inter-facet spacer 1910 into the cervical facet joint. In this embodiment, the artificial facet joint spacer or inter-facet spacer 1910 has a rounded distal end 1912. The distal end 1912 is tapered in thickness to facilitate insertion. The tapered distal end 1912 meets and is continuous with a proximal mid-section 1916 which, in this preferred embodiment, has a uniform thickness, and is connected flexibly, preferably with a hinge 1922, to the lateral mass plate 1920, as described above. The artificial facet joint spacer (or insert) or inter-facet spacer (or insert) 1910, with its proximal mid-section 1916 and tapered distal end 1912, is curved downward, causing a superior surface 1913 of the artificial facet joint spacer or inter-facet spacer 1910 to be curved. The curve can cause the superior surface 1913 to be convex, and the convexity can vary among different implants 1900 to suit the anatomical structure of the cervical facet joint(s) of a patient. An inferior surface 1915 accordingly can be preferably concave, flat, or convex. The curved shape of the implant can fit the shape of a cervical facet joint, which is comprised of an inferior facet of an upper vertebra and a superior facet of a lower adjacent vertebra. The convex shape of the superior surface 1913 of the artificial facet joint spacer or inter-facet spacer 1910 fits with a concave shape of the inferior facet of the upper cervical vertebrae. The concave shape of the inferior surface 1915 of the artificial facet joint spacer or inter-facet spacer 1910 fits with the convex shape of the superior facet of the cervical vertebrae. The degree of convexity and concavity of the artificial facet joint inferior and superior surfaces can be varied to fit a patient's anatomy and the particular pairing of adjacent cervical vertebrae to be treated. For example, a less-curved artificial facet joint spacer or inter-facet spacer 1910 can be used where the patient's cervical spinal anatomy is sized (as described below) and found to have less convexity and concavity of the articular facets. Generally for the same level the input for the right and left facet joint will be similarly shaped. It is expected that the similarity of shape of the artificial facet joint spacer or inter-facet spacer and the smooth, flush surfaces will allow distraction of the facet joint without loss of mobility or damage to the bones of the cervical spine. Further, and preferably, the width of the mid-section 1916 is from 1.5 mm to 2.5 mm.

Except as otherwise noted above, the embodiment shown in FIGS. 22A-24B is similar to the embodiment shown in FIGS. 25A, 25B. Accordingly the remaining elements on the 1900 series of element numbers is preferably substantially similar to the described elements in the 1800 series of element numbers, as set forth above. Thus, by way of example, elements 1923, 1928, 1929 and 1930 are similar to respective elements 1823, 1828, 1829 and 1830.

Figure 29A:
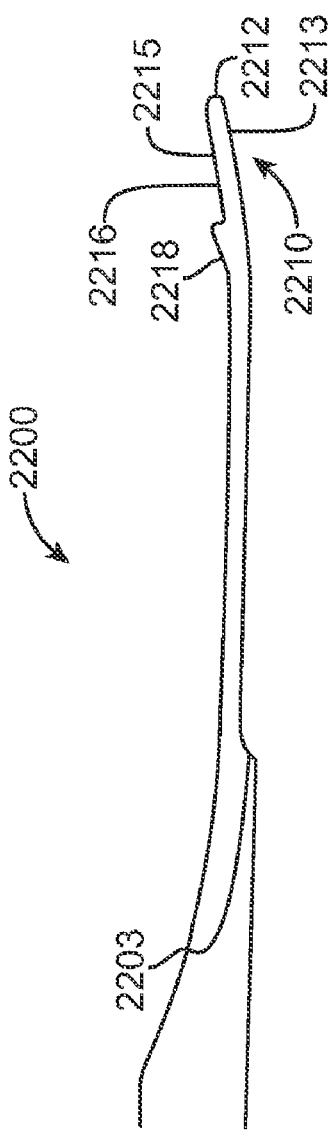
FIG. 29A depicts a side view of an embodiment of a sizing tool of the invention.
Figure 29B:
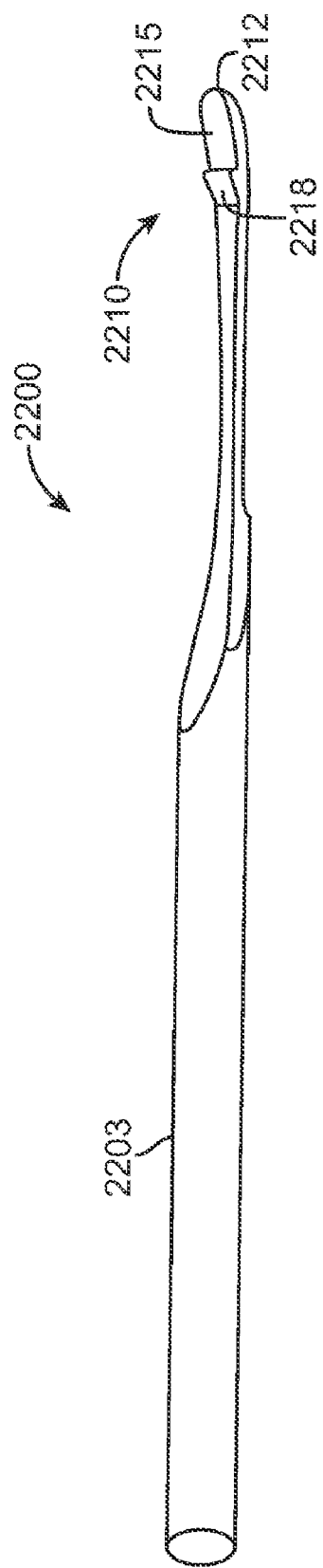
FIG. 29B depicts a top view of an embodiment of the sizing tool of the invention depicted in FIG. 29A.
Figure 29C:
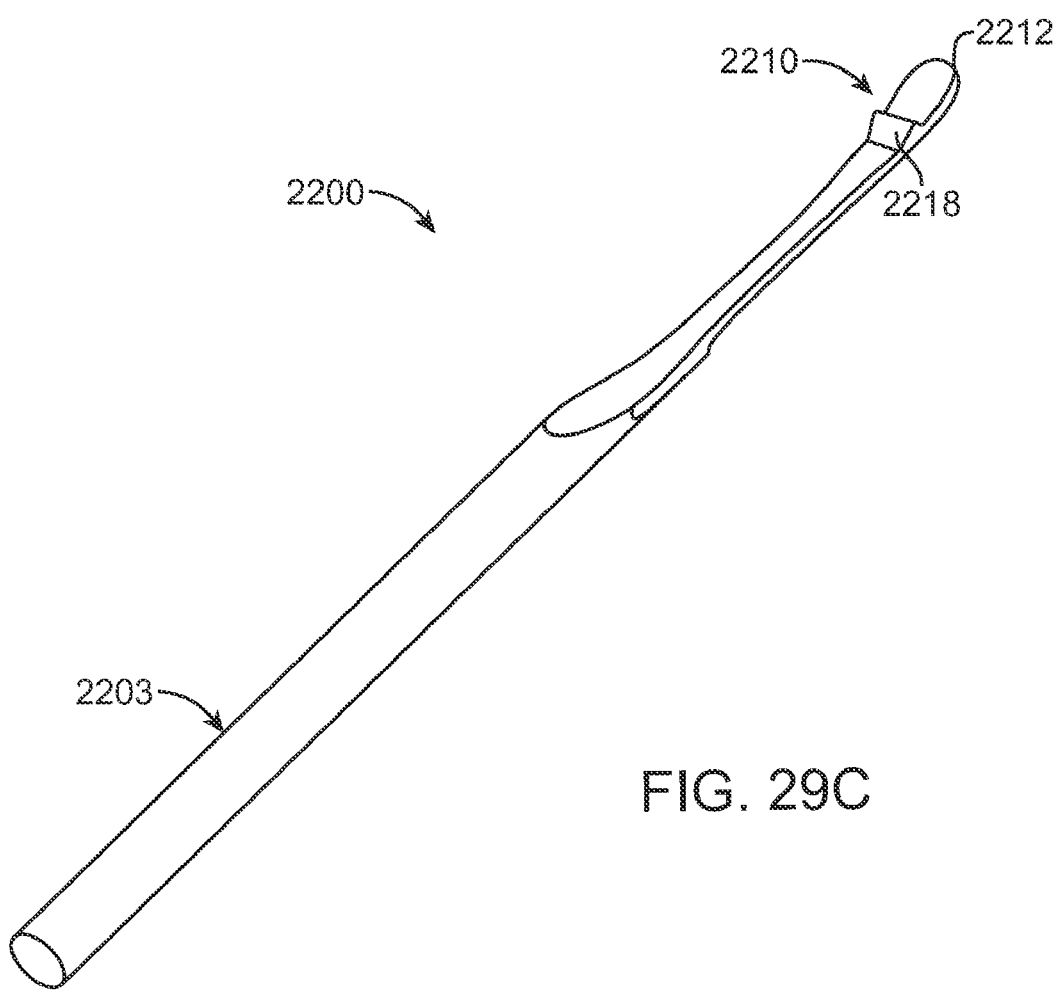
FIG. 29C depicts a perspective view of an embodiment of the sizing tool of the invention depicted in FIGS. 29A-B.
Figure 29D:
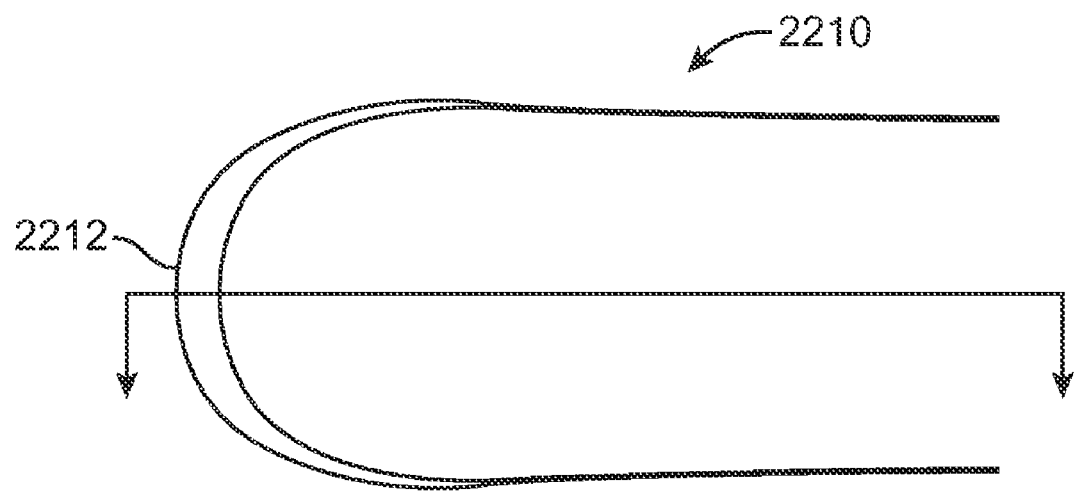
FIG. 29D depicts a side view of the head of the sizing tool of the invention depicted in FIG. 29A
Figure 29E:
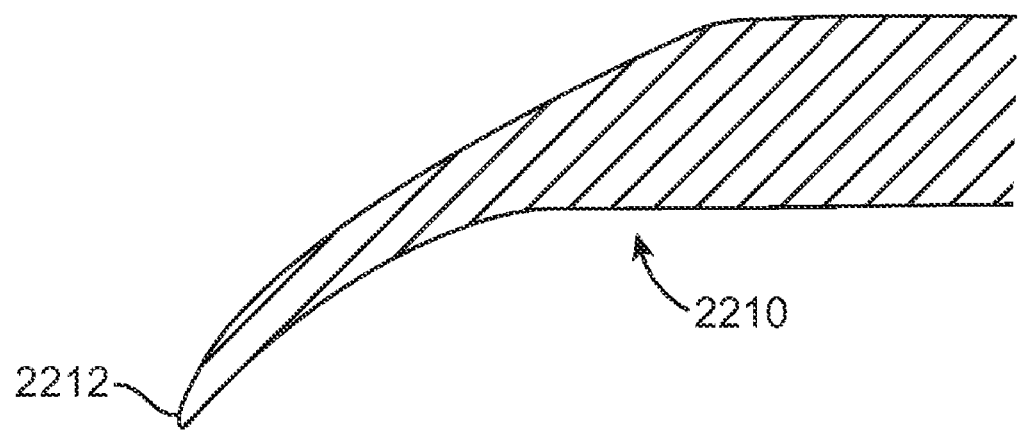
FIG. 29E depicts a cross-sectional view of the head of the sizing tool of the invention depicted in FIGS. 29A-C.
Figure 30:
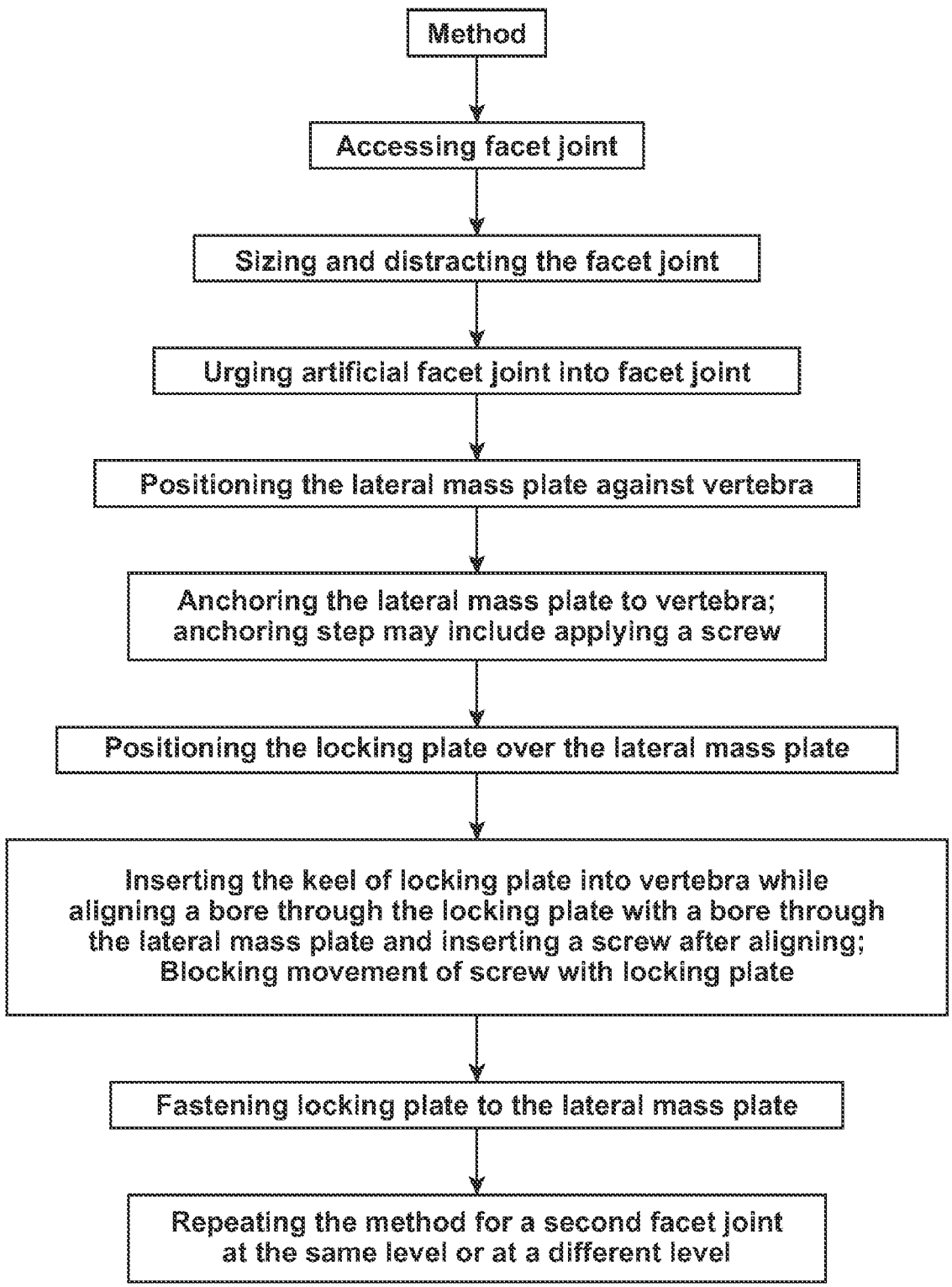
FIG. 30 is a flow diagram of an embodiment of a method of the invention.

FIG. 30 is a flow chart of the method of insertion of an implant of the invention. The embodiment 1800 or 1900 of the present invention preferably is inserted in the following manner (only elements of the embodiment 1800 will be set forth herein, for purposes of the written description of a method of the invention). First the facet joint is accessed. A sizing tool 2200 (see FIGS. 29A-C) can be inserted to select the appropriate size of an implant of the invention for positioning in the cervical facet joint. This step may be repeated as necessary with, if desired, different sizes of the tool 2200 until the appropriate size is determined. This sizing step also distracts the facet joint and surrounding tissue in order to facilitate insertion of the implant. Then, the artificial facet joint spacer or inter-facet spacer 1810 is urged between the facets into the facet joint. The facet itself is somewhat shaped like a ball and socket joint. Accordingly, in order to accommodate this shape, the artificial facet joint spacer or inter-facet spacer 1810 can have a rounded leading edge shaped like a wedge or tissue expander to cause distraction of the facet joint as the artificial facet joint spacer or inter-facet spacer is urged into the facet joint of the spine. The artificial facet joint spacer or inter-facet spacer 1810 also includes the convex surface 1813 in order to more fully accommodate the shape of the facet joint of the spine. However, as set forth above and as depicted in FIG. 25B, it is possible in the alternative to have a curve-shaped artificial facet joint spacer (or insert) or inter-facet spacer (or insert) 1910 with a convex superior surface 1913 and a concave inferior surface 1915, the distal end 1912 tapering to facilitate insertion, while the remainder of the artificial facet joint spacer or inter-facet spacer 1910, (i.e., the proximal section 1916) has a uniform thickness.

Once the artificial joint spacer or inter-facet spacer 1810 is positioned, the lateral mass plate 1820 is pivoted downward about the hinge 1822 adjacent to the vertebrae and preferably to the lateral mass or to the lamina. Thus, the lateral mass plate 1820 may be disposed at an angle relative to the artificial facet joint spacer or inter-facet spacer 1810 for a representative spine configuration. It is to be understood that as this embodiment is hinged the final position of the lateral mass plate 1820 relative to the artificial facet joint spacer or inter-facet spacer 1810 will depend on the actual spine configuration. It is to be understood that embodiments of the invention can be made without a hinge, as long as the connection between the artificial facet joint spacer or inter-facet spacer and the lateral mass plate is flexible enough to allow the lateral mass plate to be bent relative to the artificial facet joint spacer or inter-facet spacer in order to fit the anatomy of the patient. Once the lateral mass plate 1820 is positioned, or prior to the positioning of the lateral mass plate 1820, a bore can be drilled in the bone to accommodate the bone screw 1824. Alternatively the screw 1824 can be self-tapping. The screw is then placed through the bore 1830 and secured to the bone, preferably the lateral mass or the lamina, thereby holding the artificial facet joint spacer or inter-facet spacer 1810 in place. In order to lock the bone screw 1824 in place and to lock the position of the artificial facet joint spacer or inter-facet spacer 1810 and the lateral mass plate 1820 in place, the locking plate 1824 is positioned over the lateral mass plate 1820. So positioned, the probe 1826 is positioned through the bore 1830 and against the head of the bone screw to keep the bone screw from moving. The keel 1828, having a sharp chisel-shaped end, preferably can self-cut a groove in the bone so that the keel 1828 is locked into the bone as the keel 1828 is aligned by, and received in, a groove 1831 of the lateral mass plate 1820. Alternatively, a groove can be pre-cut in the bone to receive the keel 1828. As this occurs the bore 1829 of the locking plate 1824 aligns with the threaded bore 1831 of the lateral mass plate 1820 and a machine screw can be inserted to lock the locking plate relative to the lateral mass plate. This locking prevents the lateral mass plate 1820 and the artificial facet joint spacer or inter-facet spacer 1810 from rotating and, as previously indicated, prevents the bone screw 1840 from backing out from the vertebra. Preferably the implant is between the C5 and C6 vertebrae level, or the C6 and C7 vertebrae level. It is noted that two implants preferably will be implanted at each level between vertebrae. That is, an implant 1800 will be placed in a right facet joint and also in a left facet joint when viewed from a posterior view point. This procedure can be used to increase or distract the foraminal area or dimension of the spine in an extension or in neutral position (without having a deleterious effect on cervical lordosis) and reduce the pressure on the nerves and blood vessels. At the same time this procedure preserves mobility of the facet joint.

Figure 26A:
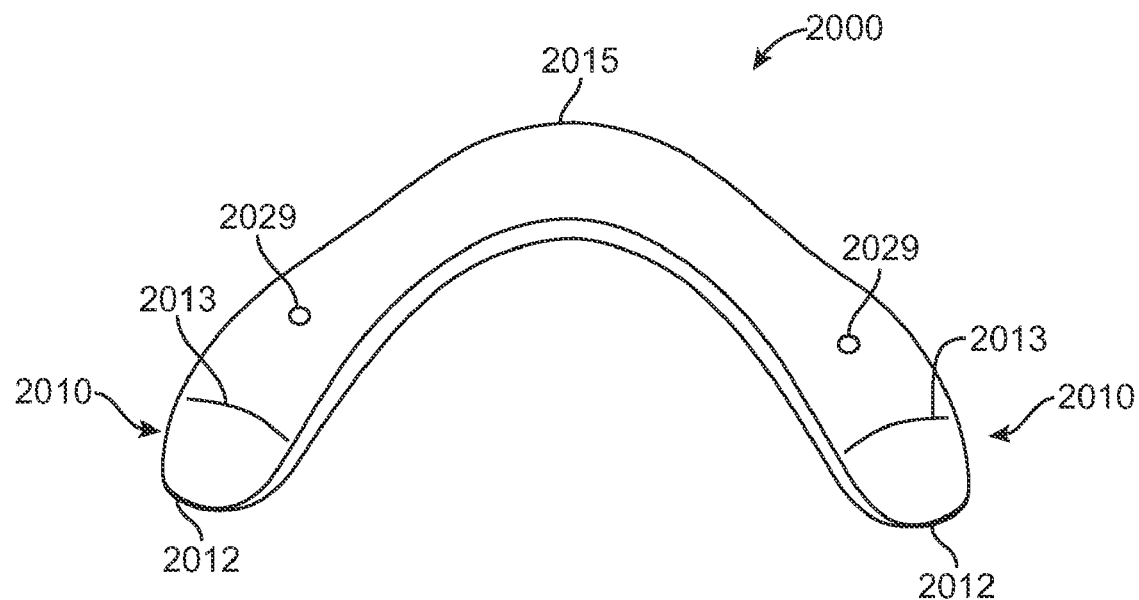
FIG. 26A shows an anterior perspective view of a further embodiment of the implant of the invention.
Figure 26B:
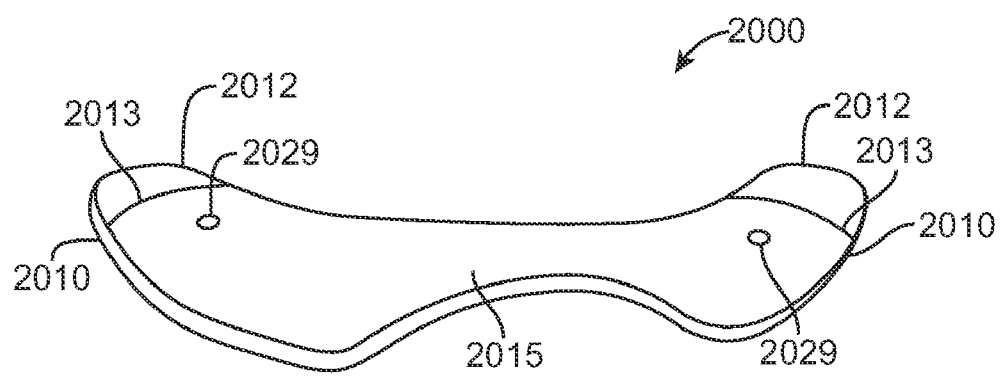
FIG. 26B shows a posterior perspective view of the embodiment of the implant of the invention depicted in FIG. 26A.
Figure 27A:
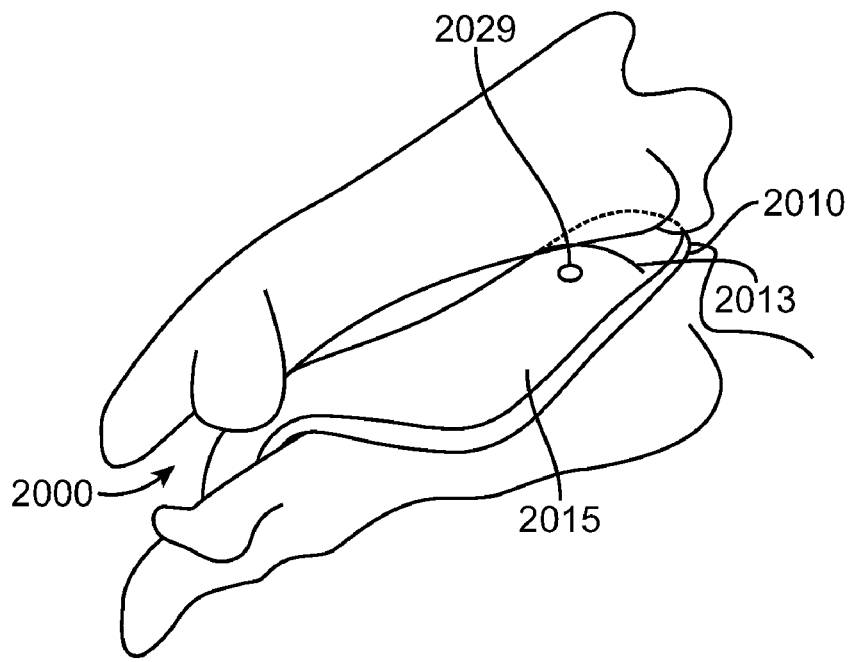
FIG. 27A depicts a side view of the embodiment of the implant of the invention shown in FIGS. 26A and 26B, implanted in the cervical spine.
Figure 27B:
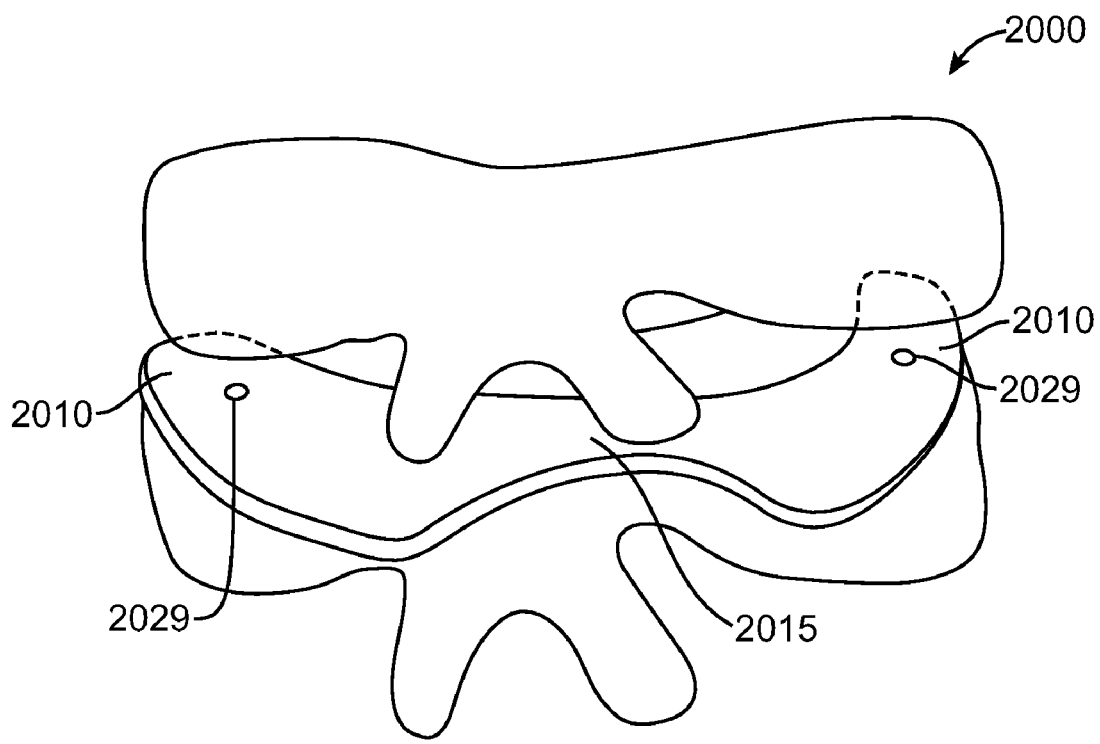
FIG. 27B shows a posterior view of the embodiment of the implant of the invention shown in FIGS. 26A, 26B, and 27A, implanted in the cervical spine.

FIGS. 26A-27B show a further embodiment of the implant of the invention, with the embodiment 2000 implanted in the cervical spine as depicted in FIGS. 27A and 27B. The implant 2000 comprises a first artificial facet joint spacer (or insert) or inter-facet spacer (or insert) 2010 and a second artificial facet joint spacer (or insert) or inter-facet spacer (or insert) 2010. Each artificial facet joint spacer or inter-facet spacer can have a distal end 2012 that is tapered or wedge-shaped in a way that facilitates insertion into the cervical facet joints on both sides of two adjacent cervical vertebrae at the same level. The artificial facet joint spacers or inter-facet spacers further can be dome-shaped, or convex on a superior surface 2013, to approximate the shape of the cervical facets of the cervical facet joints.

Figure 28A:
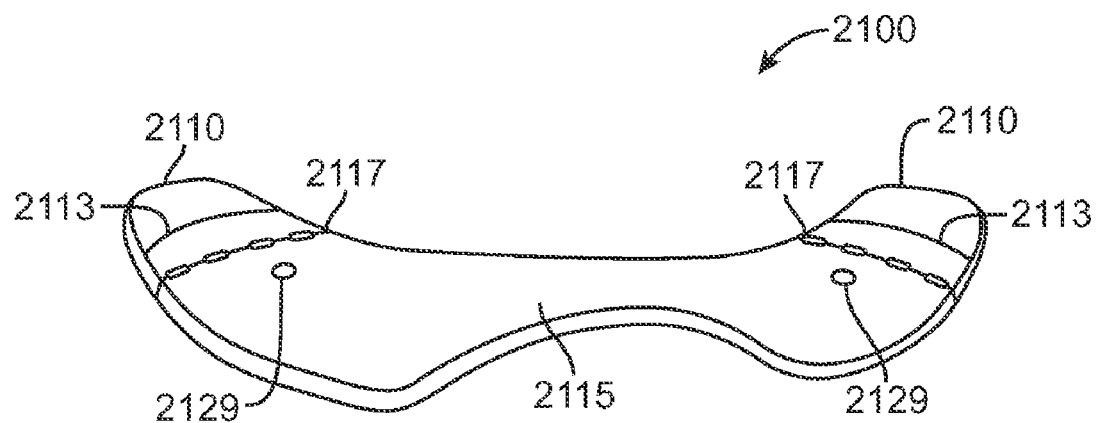
FIG. 28A depicts a posterior perspective view of a further embodiment of the implant of the invention.
Figure 28B:
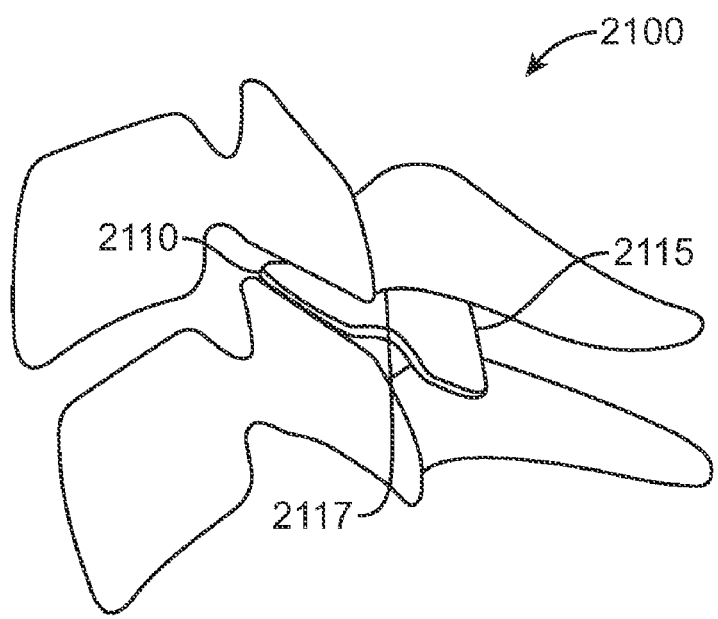
FIG. 28B depicts a side view of the embodiment of the implant of the invention shown in FIG. 28A.

The first and second artificial facet joint spacers or inter-facet spacers 2010 are bridged together by a collar 2015. The collar 2015 passes between the spinous processes of the adjacent cervical vertebrae. As can be seen in FIG. 26B, the implant can preferably be "V" shaped or "boomerang"

shaped. The entire implant 2000 or the collar 2015 of the implant can be made of a flexible material such as titanium, so that it is possible to bend the collar 2015 so that it conforms preferably to the shape of the lateral mass or the lamina of the cervical vertebrae of the patient and thereby holds the implant in place with the artificial facet joint spacers or inter-facet spacers 2010 inserted in the cervical facet joints. Bores 2029 are preferably are provided through implant 2000 adjacent to the artificial facet joint spacer or inter-facet spacer 2010 respectively. These bores 2029 can receive bone screws to position the implant 2000 against the lateral mass or the lamina as shown in FIGS. 27A, 27B. The description of the embodiment 2100, in FIGS. 28A, 28B provide further details concerning the method of affixing the implant 2000 to the vertebrae. The implant 2100 also can be made of PEEK or other materials as described herein. Embodiment 2000 (the "boomerang" shape depicted in FIG. 27B) further can have a locking plate as, for example, the locking plate 1824 in FIG. 22A. The locking plate for embodiment 2000 (not shown) can have the same features as locking plate 1824, that is: (1) a probe 1826 that interacts with the bone screws to prevent the bone screws from backing out of the bone, the likely consequence of which would be displacement of the implant 2000; and (2) a keel 1828 with a chisel end to embed in the bone and thus to prevent rotational displacement of the implant. However, given the collar 2015 configuration of embodiment 2000, a chisel may not serve the same purpose as with the embodiments set forth above, which lack a collar stabilized by two bone screws. Therefore, a locking plate on embodiment 2000 can be provided without a keel.

FIGS. 28A and 28B depict a further embodiment of the implant of the invention 2100. In this embodiment 2100, the collar 2115 can be made of a flexible material such as titanium, of a substantially inflexible material, or of other materials described herein. Substantial flexibility can also be derived from connecting a first artificial facet joint spacer or inter-facet spacer 2110 with the collar 2115 using a first hinge 2117, and connecting a second artificial facet joint spacer or inter-facet spacer 2110 with the collar 2115 using a second hinge 2117. Using the first hinge 2117 and the second hinge 2117, the collar 2115 can be pivoted downward to conform to a particular patient's cervical spinal anatomy. In other words, the degree of pivoting will vary among different patients, and the first hinge 2117 and second hinge 2117 allow the implant 2100 to accommodate the variance.

In the hinged embodiment 2100, and similar to the embodiment 2000, the collar 2115 can have a first bore 2129 inferior to the first hinge 2117, and a second bore 2129 inferior to the second hinge 2117. A first bone screw penetrates the first bore 2130 and into the lateral mass or the lamina, and the second bone screw penetrates the second bore 2130 and into the lateral mass or the lamina, the first and second bone screws serving to anchor the implant. A bore, preferably in the lateral mass, can be drilled for the first bone screw and for the second bone screw. Alternatively, the bone screws can be self-tapping. A first locking plate similar to the plate 1924 (FIG. 25A) can be secured about the head of the first bone screw and a second locking plate can be secured about the head of the second bone screw to prevent displacement of the first and second bone screws 2140. The first locking plate can block the first bone screw with a probe and the second locking plate can block to the second bone screw with a probe.

It should be noted that embodiments 2000 and 2100 also can be configured for accommodating treatment of cervical spinal stenosis and other cervical spine ailments where only a single cervical facet joint between adjacent vertebrae requires an implant, i.e., where treatment is limited to one lateral facet joint. In that case, the collar 2015, 2115 extends medially without extending further to join a second artificial facet joint spacer or inter-facet spacer 2010, 2110. For the hinged embodiment 2100, the implant comprises a single hinge 2117, and the collar 2115 has only one bore 2129 to accept one bone screw to secure the implant 2100.

FIGS. 29A-E, depict a sizing and distracting tool 2200 of the invention. Sizing tool 2200 has a handle 2203 and a distal head 2210 that is shaped as an artificial facet joint spacer or inter-facet spacer (e.g., 1810) of an implant of the invention. That is, the head 2210 preferably will have essentially the same features as the artificial facet joint spacer or inter-facet spacer 1810, but the dimensions of the head 2210 will vary from one tool 2200 to the next, in order to be able to use different versions of the sizing tool 2200 to determine the dimensions of the cervical facet joint that is to be treated and then to select an appropriately-sized implant. The head 2210 preferably can be used to distract the facet joint prior to the step of implanting the implant in the facet joint. In this regard, the head 2210 is rounded at the most distal point 2212, and can be a tapered to facilitate insertion into a cervical facet joint. The head 2210 also can have a slightly convex superior surface 2213, the degree of convexity varying among different sizing tools 2200 in order to determine the desired degree of convexity of an implant to be implanted in the cervical facet joint. The head 2210 may have a uniform thickness along a proximal mid-section 2216. Accordingly, the inferior surface 2215 preferably can be concave. Alternatively, the proximal mid-section 2212 may be convex on the superior surface 1813 without being uniform in thickness. Thus, the inferior surface 2215 can be flat or planar. The head also can be curved.

The head 2210 has a stop 2218 to prevent over-insertion of the head 2210 of the sizing tool 2200 into the facet joint. The stop 2218 can be a ridge that separates the head 2210 from the handle 2203. Alternatively, the stop 2218 can be any structure that prevents insertion beyond the stop 2218, including pegs, teeth, and the like.

Different sizing tools 2200 covering a range of dimensions of the head 2210 can be inserted successively into a cervical facet joint to select the appropriate size of an implant to position in the cervical spine, with the appropriate convexity and concavity of artificial facet joint. Each preferably larger head also can be used to distract the facet joint.

The foregoing description of the present invention has been presented for purposes of illustration and description. It is not intended to be exhaustive or to limit the invention to the precise forms disclosed. Many modifications and variations will be apparent to practitioners skilled in this art. The embodiments were chosen and described in order to explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A facet joint implant adapted to correct spinal stenosis and other ailments of the spine without eliminating mobility of the facet joint, the implant comprising:
    a facet joint spacer adapted to be positioned in a spinal facet joint and to distract the spinal facet joint, wherein the distraction causes an increase in foraminal dimension, the facet joint spacer having a connection with a first plate;
    said first plate adapted to be anchored to a vertebra; and
    a second plate including a probe that extends into the anchored first plate, the second plate having a keel that protrudes so as to penetrate the vertebra outside the spinal facet joint as the second plate is fastened to the anchored first plate, wherein the penetration of the vertebra by the keel prevents the first plate and the second plate from rotating.

2. The facet joint implant as in claim 1 wherein said connection includes a hinge.

3. The facet joint implant as in claim 1 wherein the first plate further comprises a first bore, the first bore and a first screw accepted through said first bore to anchor the implant to a vertebra.

4. The facet joint implant as in claim 3 wherein the second plate further comprises a block, said block to interfere with movement of the first screw with the first plate and the second plate positioned adjacent to each other.

5. The facet joint implant as in claim 1 wherein the artificial facet joint is tapered so as to be adapted to cause distraction of the facet joint as the facet joint spacer is urged into the facet joint.

6. The facet joint implant as in claim 1 wherein the facet joint spacer is convex on a surface in order to be adapted to accommodate the shape of a cervical facet joint.

7. The facet joint implant as in claim 1 wherein the facet joint spacer is disposable at an angle greater than 90 degrees relative to the first plate.

8. The facet joint implant as in claim 1 wherein the connection between the facet joint spacer and the first plate is flexible.

9. The facet joint implant as in claim 1 wherein the keel includes an edge and is adapted to self-cut a groove in the lateral mass.

10. The cervical facet joint implant as in claim 1 wherein the implant does not require resection of any bone.

11. The implant of claim 1 wherein said second plate is received in a recess of said first plate such that the second plate is flush with the first plate.

12. The implant of claim 1 wherein the facet joint spacer comprises a material that promotes bone ingrowth.

13. A facet joint implant adapted to correct spinal stenosis and other ailments of the spine without eliminating mobility of the facet joint, the implant comprising:
   a first plate having a first bore and adapted to anchor to a vertebra with the first bore and a first screw accepted through said first bore to anchor the implant to a vertebra;
   a facet joint spacer adapted to be positioned in a spinal facet joint and to distract the spinal facet joint, wherein the distraction causes an increase in foraminal dimension, the facet joint spacer having a connection with a first plate;
   a second plate that fastens to the first plate, the second plate having a keel adapted to penetrate the vertebra, wherein the penetration of the vertebra by the keel prevents the first plate and the second plate from rotating;
   a second bore through the first plate;
   a third bore through the second plate that aligns with second bore on the first plate when the keel is implanted in the vertebra and the second plate and the first plate are positioned to be fastened together; and
   a second screw accepted through the aligned second bore and third bore, the second screw to fasten the first plate with the second plate and prevent rotation of the first plate and the second plate relative to each other.

14. A cervical facet joint implant adapted to correct cervical spinal stenosis and other ailments of the cervical spine, the implant comprising:
   a facet joint spacer adapted to be inserted into and to distract a cervical facet joint, wherein the distraction increases the foraminal dimension without eliminating mobility of the cervical facet joint;
   a hinge connecting the facet joint spacer with a lateral mass plate;
   the lateral mass plate adapted to be positioned against the lateral mass of the vertebra, the lateral mass plate having a first bore and a second bore;
   a bone screw accepted by the first bore and adapted to penetrate the lateral mass to anchor the implant, the bone screw having a head;
   a locking plate that mates with the lateral mass plate to prevent rotation of the lateral mass plate, the locking plate further comprising:
      a keel, said keel adapted to penetrate the vertebra and anchor the implant to the vertebra; and
      a third bore that aligns with the second bore, and wherein the second and third bores accept a second screw therethrough to join the lateral mass plate and the locking plate.

15. The cervical facet joint implant as in claim 14 wherein the second plate further comprises a block that blocks the bone screw positioned in the facet joint spacer, with the lateral mass plate and the locking plate positioned adjacent each other.

16. The cervical facet joint implant as in claim 14 including a first said implant is adapted to be positioned in a first lateral cervical facet joint formed by two adjacent vertebrae, and a second said implant is adapted to be positioned in a second lateral facet joint formed by the two adjacent vertebrae.

17. The cervical facet joint implant as in claim 14 wherein the keel has a chisel-shaped end for self-cutting a groove in the vertebra.

18. The cervical facet joint implant as in claim 14 wherein the lateral mass plate further comprises a groove that accepts the keel of the locking plate, said groove adapted to guide the keel as the keel cuts into the vertebra.

19. The cervical facet joint implant as in claim 14 wherein the facet joint spacer has a tapered distal end, the tapered distal end to facilitate insertion.

20. The cervical facet joint implant as in claim 14 wherein the facet joint spacer has a convex surface to approximate the shape of the cervical facet joint.

21. The cervical facet joint implant as in claim 14 wherein the facet joint spacer comprises a material that promotes bone ingrowth.

* * * * *

UNITED STATES PATENT AND TRADEMARK OFFICE
CERTIFICATE OF CORRECTION

| | | |
|---|---|---|
| PATENT NO. | : 7,591,851 B2 | Page 1 of 1 |
| APPLICATION NO. | : 11/053399 | |
| DATED | : September 22, 2009 | |
| INVENTOR(S) | : Winslow et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 525 days.

Signed and Sealed this

Twenty-first Day of September, 2010

David J. Kappos
*Director of the United States Patent and Trademark Office*